United States Patent
Ho et al.

(10) Patent No.: US 9,301,927 B2
(45) Date of Patent: Apr. 5, 2016

(54) PARA-XYLENE FILMS AND THERAPEUTIC USES THEREOF

(71) Applicants: Northwestern University, Evanston, IL (US); ANN & ROBERT H. LURIE CHILDREN'S HOSPITAL OF CHICAGO, Chicago, IL (US); UNIVERSITY OF MARYLAND, BALTIMORE, Baltimore, MD (US)

(72) Inventors: Dean Ho, Los Angeles, CA (US); Erik M. Robinson, Chicago, IL (US); Sunjay Kaushal, Pikesville, MD (US); Patrick M. McCarthy, Winnetka, IL (US)

(73) Assignees: Northwestern University, Evanston, IL (US); University of Maryland, Baltimore, Baltimore, MD (US); Ann & Robert H. Lurie Children's Hospital of Chicago, Chicago, IL (US)

( * ) Notice: Subject to any disclaimer, the term of this patent is extended or adjusted under 35 U.S.C. 154(b) by 0 days.

(21) Appl. No.: 14/283,819

(22) Filed: May 21, 2014

(65) Prior Publication Data

US 2014/0348895 A1 Nov. 27, 2014

Related U.S. Application Data

(60) Provisional application No. 61/825,775, filed on May 21, 2013.

(51) Int. Cl.
*A61L 31/06* (2006.01)
*A61L 31/08* (2006.01)
*A61L 31/10* (2006.01)
*C08L 65/04* (2006.01)
*A61L 29/08* (2006.01)
*A61K 9/70* (2006.01)

(52) U.S. Cl.
CPC ............. *A61K 9/7007* (2013.01); *A61L 29/085* (2013.01); *A61L 31/06* (2013.01); *A61L 31/082* (2013.01); *A61L 31/10* (2013.01)

(58) Field of Classification Search
None
See application file for complete search history.

(56) References Cited

U.S. PATENT DOCUMENTS

| 8,709,467 B2 | 4/2014 | Pierstorff et al. |
| 2008/0220169 A1 | 9/2008 | Khademhosseini et al. |
| 2010/0080957 A1 | 4/2010 | Chinn et al. |
| 2011/0293666 A1* | 12/2011 | Wang et al. ............... 424/400 |
| 2012/0135061 A1 | 5/2012 | Pierstorff et al. |

FOREIGN PATENT DOCUMENTS

| WO | WO 94/08635 | * 4/1994 |
| WO | WO 2014/190047 | 11/2014 |

OTHER PUBLICATIONS

Alizzi, A.M. et al. Reduction of Post-surgical Pericardial Adhesions Using a Pig Model. Heart Lung and Circulation 21, 22-29 (2012).

Alpay, Z. et al. Altered in vitro immune response to hypoxia-treated normal peritoneal fibroblasts. Fertility and Sterility 87, 426-429 (2007).

Andersson, A.S. et al. Nanoscale features influence epithelial cell morphology and cytokine production. Biomaterials 24, 3427-3436 (2003).

Aviles, R.J. et al. Inflammation as a risk factor for atrial fibrillation. Circulation 108, 3006-3010 (2003).

Bagshaw, S.M. et al. Prophylactic amiodarone for prevention of atrial fibrillation after cardiac surgery: A meta-analysis. Annals of Thoracic Surgery 82, 1927-1937 (2006).

Beck et al., A Prospective, Randomized, Multicenter, Controlled Study of the Safety of Seprafilm® Adhesion Barrier in Abdominopelvic Surgery of the Intestine, Dis Colon Rectum, 46, 1310-1319 (2003).

Bellon et al., Evaluation of the acute scarring response to the implant of different types of biomaterial in the abdominal wall, J Mater Sci Mater Med, 11, 25-29 (2000).

Bellon et al., The structure of a biomaterial rather than its chemical composition modulates the repair process at the peritoneal level, Am J Surg, 184, 154-159 (2002).

Bellon et al., In vitro mesothelialization of prosthetic materials designed for the repair of abdominal wall defects, J Mater Sci Mater Med, 14, 359-364 (2003).

Bellows et al., Abdominal wall reconstruction using biological tissue grafts: present status and future opportunities, Expert Rev Med Devices, 3, 657-675 (2006).

Binnebosel et al., Biocompatibility of prosthetic meshes in abdominal surgery, 33, 235-243 (2011).

Boduroglu, S. et al. Controlling the Wettability and Adhesion of Nanostructured Poly-(p-xylylene) Films. Langmuir 23, 11391-11395 (2007).

(Continued)

*Primary Examiner* — David J Blanchard
*Assistant Examiner* — Sarah Chickos
(74) *Attorney, Agent, or Firm* — Casimir Jones, S.C.

(57) ABSTRACT

The present invention provides single sheet and compound para-xylene films for therapeutic uses. For example, the present invention provides single sheet para-xylene films useful as tissue separators and/or adhesion barriers in a subject, where the top and/or bottom surfaces of such films have a water contact angle between 75 and 95 degrees (e.g., to prevent adhesion formation). The present invention also provides compound films composed of at least two para-xylene polymer films with a therapeutic molecule layer in between. Such compound films, when used in vivo (e.g., as a tissue separator and to treat inflammation or atrial fibrillation) allow either therapeutic molecule elution through one of the para-xylene layers, or therapeutic molecule release when the compound film is pierced, such as when it is sutured in place.

14 Claims, 9 Drawing Sheets

(56) References Cited

OTHER PUBLICATIONS

Bolderman, R.W. et al. Epicardial application of an amiodarone-releasing hydrogel to suppress atrial tachyarrhythmias. International Journal of Cardiology 149, 341-346 (2011).

Burger et al, Evaluation of new prosthetic meshes for ventral hernia repair, Surg Endosc, 20, 1320-1325 (2006).

Chang, Y. et al. Mesothelium regeneration on acellular bovine pericardia loaded with an angiogenic agent (ginsenoside Rg(1)) successfully reduces postsurgical pericardial adhesions. Journal of Thoracic and Cardiovascular Surgery 132, 867-U874 (2006).

Chen, M. et al. Parylene-Encapsulated Copolymeric Membranes as Localized and Sustained Drug Delivery Platforms. Annals of Biomedical Engineering 37, 2003-2017 (2009).

Cheong, Y.C. et al. Peritoneal healing and adhesion formation/reformation. Human Reproduction Update 7, 556-566 (2001).

Davey et al., Surgical adhesions: A timely update, a great challenge for the future, J Minim Invasive Gynecol, 14, 15-22 (2007).

Deftereos, S. et al. Colchicine for Prevention of Early Atrial Fibrillation Recurrence After Pulmonary Vein Isolation a Randomized Controlled Study. Journal of the American College of Cardiology 60, 1790-1796 (2012).

Diamond et al., Adhesion prevention and reduction: current status and future recommendations of a multinational interdisciplinary consensus conference, Surg Innov, 17, 183-188 (2010).

diZeregal, G.S. & Campeau, J.D. Peritoneal repair and post-surgical adhesion formation. Human Reproduction Update 7, 547-555 (2001).

Dowling et al., Effect of Surface Wettability and Topography on the Adhesion of Osteosarcoma Cells on Plasma-modified Polystyrene, J Biomater Appl, 26, 327-347 (2010).

Emans et al., Polypropylene Meshes to Prevent Abdominal Herniation. Can Stable Coatings Prevent Adhesions in the Long Term?, Annals of Biomedical Engineering, 37, 410-418 (2009).

Epstein et al., Human Peritoneal Adhesions Show Evidence of Tissue Remodeling and Markers of Angiogenesis, Dis Colon Rectum, 49, 1885-1892 (2006).

Ferrando et al., Experimental Evaluation of a New Layered Prosthesis Exhibiting a Low Tensile Modulus of Elasticity: Long-term Integration Response within the Rat Abdominal Wall, World J Surg., 26, 409-415 (2002).

Gruber-Blum et al., Comparison of three separate antiadhesive barriers for intraperitoneal onlay mesh hernia repair in an experimental model, British Journal of Surgery, 98, 442-449 (2011).

Guo, Y., Lip, G.Y.H. & Apostolakis, S. Inflammation in Atrial Fibrillation. Journal of the American College of Cardiology 60, 2263-2270 (2012).

Halonen, J. et al. Corticosteroids for the prevention of atrial fibrillation after cardiac surgery—A randomized controlled trial. Jama-Journal of the American Medical Association 297, 1562-1567 (2007).

Harris et al., Analysis of the kinetics of peritoneal adhesion formation in the rat and evaluation of potential antiadhesive agents, Surgery, 117, 663-669 (1995).

Hellebrekers et al., Effects of five different barrier materials on post-surgical adhesion formation in the rat, Hum Reprod, 15, 1358-1363 (2000).

Horcas, I. et al. WSXM: A software for scanning probe microscopy and a tool for nanotechnology. Review of Scientific Instruments 78 (2007).

Imazio, M. et al. Colchicine prevents early postoperative pericardial and pleural effusions. American Heart Journal 162, 527-U149 (2011).

Imazio, M. et al. Colchicine Reduces Postoperative Atrial Fibrillation Results of the Colchicine for the Prevention of the Postpericardiotomy Syndrome (COPPS) Atrial Fibrillation Substudy. Circulation 124, 2290-U2258 (2011).

Jeong et al., UV—visible and infrared characterization of poly(p-xylylene) films for waveguide applications and OLED encapsulation, Synthetic Metals, 127, 189-193 (2002).

Jin et al., Human Peritoneal Membrane Controls Adhesion Formation and Host Tissue Response Following Intra-Abdominal Placement in a Porcine Model, J Surg Res, 156, 297-304 (2009).

Koehler et al., Minimal Adhesions to ePTFE Mesh After Laparoscopic Ventral Incisional Hernia Repair: Reoperative Findings in 65 Cases, JSLS, 7, 335-340 (2003).

Lam et al., "Nanodiamond-Embedded Microfilm Devices for Localized Chemotherapeutic Elution," Acs Nano 2, 2008, 2095-2102.

Lim et al., Practical Limitations of Bioresorbable Membranes in the Prevention of Intra-Abdominal Adhesions, J Gastrointest Surg, 13, 35-42 (2009).

Lin, C.-C., Metters, A.T. & Anseth, K.S. Functional PEG—peptide hydrogels to modulate local inflammation inducedby the pro-inflammatory cytokine TNFα. Biomaterials 30, 4907-4914 (2009).

Lodge, A.J. et al. A Novel Bioresorbable Film Reduces Postoperative Adhesions After Infant Cardiac Surgery. The Annals of Thoracic Surgery 86, 614-621 (2008).

Luijendijk et al., A Comparison of Suture Repair With Mesh Repair for Incisional Hernia, NEJM, 343, 392-398 (2000).

Matthews et al., Assessment of Adhesion Formation to Intra-Abdominal Polypropylene Mesh and Polytetrafluoroethylene Mesh, J Surg Res, 114, 126-132 (2003).

Matthews et al., Evaluation of Adhesion Formation and Host Tissue Response to Intra-abdominal Polytetrafluoroethylene Mesh and Composite Prosthetic Mesh, J Surg Med, 123, 227-234 (2005).

Mitchell, J., Lee, R., Neya, K. & Vlahakes, G. Reduction in experimental pericardial adhesions using a hyaluronic acid bioabsorbable membrane. Eur J Cardiothorac Surg 8, 149-152 (1994).

Mohiuddin, M., Pan, H.-A., Hung, Y.-C. & Huang, G.S. Control of growth and inflammatory response of macrophages and foam cells with nanotopography. Nanoscale Research Letters 7, 1-9 (2012).

Pierstorff et al., "Nanoscale architectural tuning of parylene patch devices to control therapeutic release rates," Nanotechnology, 2008, 19:1-8.

Price, J.D., Romeiser, J.L., Gnerre, J.M., Shroyer, A.L.W. & Rosengart, T.K. Risk Analysis for Readmission after Coronary Artery Bypass Surgery: Developing a Strategy to Reduce Readmissions. Journal of the American College of Surgeons.

Riet et al., Prevention of Adhesion to Prosthetic Mesh: Comparison of Different Barriers Using an Incisional Hernia Model, Annals of Surgery, 237, 123-128 (2003).

Robinson, E.M., Lam, R., Pierstorff, E.D. & Ho, D. Localized Therapeutic Release via an Amine-Functionalized Poly-p-xylene Microfilm Device. The Journal of Physical Chemistry B 112, 11451-11455 (2008).

Ryan et al., Postoperative Peritoneal Adhesions, Am J Pathol, 65, 117-139.

Saed, G.M. & Diamond, M.P. Apoptosis and proliferation of human peritoneal fibroblasts in response to hypoxia. Fertility and Sterility 78, 137-143 (2002).

Saed, G.M. & Diamond, M.P. Hypoxia-induced irreversible up-regulation of type I collagen and transforming growth factor-beta 1 in human peritoneal fibroblasts. Fertility and Sterility 78, 144-147 (2002).

Saed, G.M. & Diamond, M.P. Molecular Characterization of Postoperative Adhesions: The Adhesion Phenotype. The Journal of the American Association of Gynecologic Laparoscopists 11, 307-314 (2004).

Saed, G.M., Zhang, W. & Diamond, M.P. Molecular characterization of fibroblasts isolated from human peritoneum and adhesions. Fertility and Sterility 75, 763-768 (2001).

Sakuma, K., Iguchi, A., Ikada, Y. & Tabayashi, K. Closure of the pericardium using synthetic bioabsorbable polymers. Annals of Thoracic Surgery 80, 1835-1840 (2005).

Santucci et al., Vapor phase surface functionalization under ultra violet activation of parylene thin films grown by chemical vapor deposition, Thin Solid Films, 518, 1675-1681 (2010).

Schreiber, C. et al. European clinical experience with REPEL-CV (R). Expert Review of Medical Devices 4, 291-295 (2007).

Schreinemacher et al., Degradation of mesh coatings and intraperitoneal adhesion formation in an experimental model, British Journal of Surgery, 96, 305-313 (2009).

(56) References Cited

OTHER PUBLICATIONS

Song et al., Improved Biocompatibility of Parylene-C Films Prepared by Chemical Vapor Deposition and the Subsequent Plasma Treatment, J Appl Polymer Sci, 112, 3677-3685 (2009).

Speir et al., Additive Costs of Postoperative Complications for Isolated Coronary Artery Bypass Grafting Patients in Virginia. Annals of Thoracic Surgery 88, 40-46 (2009).

Stevenson et al., Reservoir-based drug delivery systems utilizing microtechnology. Advanced Drug Delivery Reviews 64, 1590-1602 (2012).

Sun, Q. et al. Sustained Release of Multiple Growth Factors from Injectable Polymeric System as a Novel Therapeutic Approach Towards Angiogenesis. Pharm Res 27, 264-271 (2010).

Tingstedt et al., Prevention of Abdominal Adhesions—Present State and What's beyond the Horizon?, Eur Surg Res, 39, 259-268 (2007).

Townsend et al., A Novel Hydrogel-Coated Polyester Mesh Prevents Postsurgical Adhesions in a Rat Model, J Surg Res, 167, e117-e124 (2011).

Vrijland et al., Fewer Intraperitoneal Adhesions With Use of Hyaluronic Acid—Carboxymethylcellulose Membrane, Annals of Surgery, 235, 193-199 (2002).

Walther, T. et al. A novel adhesion barrier facilitates reoperations in complex congenital cardiac surgery. Journal of Thoracic and Cardiovascular Surgery 129, 359-363 (2005).

Ward et al., Abdominal Adhesions: Current and Novel Therapies, J Surg Res, 165, 91-111 (2011).

International Search Report and Written Opinion for PCT/US2014/038955, mailed Sep. 12, 2014, 12 pages.

\* cited by examiner

PARA-XYLENE FILMS AND THERAPEUTIC
USES THEREOF

The present application claims priority to U.S. application Ser. No. 61/825,775 filed May 21, 2013, which is herein incorporated by reference in its entirety.

FIELD OF THE INVENTION

The present invention provides for a tunable non-adherent and/or adherent single sheet, film or coating compounds comprising or consisting of para-xylene derived polymers for therapeutic uses.

BACKGROUND

Post surgical adhesions are generally fibrous bands that form between tissues and organs as a result of surgery. They may be thought of as internal scar tissue that connect tissues not normally connected, or connect permanent or resorbable implants to adjacent tissue and/or organ surfaces in a manner which is detrimental to device and/or organ function, and/or internal tissue, organ, or organ system spatial arrangement. Incorporation or integration of permanent implants to a specific tissue surface or organ may be desired however.

Adhesions form as a natural part of the body's healing process after surgery in the same way that a scar forms. The term adhesion is generally applied when the scar extends from within one tissue across to another, usually across a virtual space such as the peritoneal or thoracic cavity. As part of the process, the body deposits fibrin onto injured tissues. The fibrin acts like a glue to seal the injury and builds the fledgling adhesion, said at this point to be "fibrinous." In body cavities such as the peritoneal, pericardial and synovial cavities, a family of fibrinolytic enzymes may act to limit the extent of the initial fibrinous adhesion, and may even dissolve it. In many cases however the production or activity of these enzymes are compromised because of injury, and the fibrinous adhesion persists. If this is allowed to happen, tissue repair cells such as macrophages, fibroblasts and blood vessel cells, penetrate into the fibrinous adhesion, and lay down collagen and other matrix substances to form a permanent fibrous adhesion. While some adhesions do not cause problems, others can prevent muscle and other tissues and organs from moving freely, sometimes causing organs to become twisted or pulled from their normal positions.

Adhesions can form in the thoracic cavity, such as after cardiac surgery or related procedures. After cardiac surgery, inflammation from surgical trauma triggers adverse events. These include fluid retention, weight gain, pleural or pericardial effusions, pulmonary congestion, pericarditis, "postcardiotomy syndrome," and new-onset atrial fibrillation (with the potential for hemodynamic compromise and stroke).[1-4] In addition, the length of hospitalization as well as the utilization of medical resources may be increased (such as the need for pleural effusion drainage and therapy for atrial fibrillation), and patients are at increased risk for readmission. These complications and treatments may add significantly to the cost of care. Medical therapies to prevent these complications have had only modest success.[5-8] Therapies targeted to inhibit adhesions and the inflammatory response are needed.

SUMMARY OF THE INVENTION

In certain embodiments, the present invention provides for a transparent tunable non-adherent and/or adherent single sheet, film or coating compounds comprising or consisting of non-degradable/non-resorbable para-xylene derived polymers for therapeutic uses (e.g., to modulate cell and/or tissue response through interaction/adherence and/or integration to said polymer surface and act as a drug delivery platform).

In certain embodiments, the present invention provides for a tunable non-adherent and/or adherent single sheet, film or coating compound comprising, consisting essentially of, or consisting of para-xylene derived polymers (e.g., for therapeutic uses). For example, the present invention provides single sheet/film and/or coating of para-xylene polymer(s) useful as tissue separators, tissue adherent platforms and/or adhesion barriers in a subject, where the top and/or bottom surfaces of such films and/or coatings have a tunable chemical structure containing predominately carbon related groups, aliphatic compounds, including, but not limited to, aromatic hydrocarbons with a benzene derived backbone varying oxygen or nitrogen content to either prevent or promote cell or tissue adherence to said film or coating. Tuning of surface chemical content lend to a variety of applications where certain anti-adhesive and/or adhesive characteristics can be employed either as a film or as a coating, with thickness ranging from about 1 μm to 75 μm, or from 0.1 um to 0.2 mm (e.g., 0.1 um . . . 1 um . . . 50 um . . . 0.1 mm . . . 0.2 mm) to prevent common post-surgical complications relating to, for example, scarring, surgical adhesion, bowel obstruction, and any number of hernia or herniation related disorders.

In particular embodiments, anti-adherent surfaces are characterized by Carbon (C) and Oxygen (O) content of para-xylene surfaces with C to O ratios ranging from about 2:1 to 18:1, and/or water contact angles of 75-95 and/or surface roughness values of 1.0-10.0 nm.

In other embodiments, adherent para-xylene surfaces are characterized by a decrease in water contact angles ranging from about 1-75, roughness values of 1.0-10.0 nm, and resultant variation in C to O ratios less than 2:1 (e.g., through oxidative etching of the surface resulting in the formation of predominantly carbonyl groups, to a lesser extent carboxyl groups, and/or incorporation of nitrogen containing groups which will elicit a strong adherence and incorporation of cellular and tissue surfaces to said para-xylene sheet/film and/or surface/coating). The present invention also provides compound films composed of at least two para-xylene polymer films with a therapeutic molecule layer and/or wireless device and/or sensor in between. Such compound films, when used in vivo (e.g., as a tissue separator and to treat inflammation or atrial fibrillation) allow either therapeutic molecule elution through one of the para-xylene layers, and/or therapeutic molecule release when the compound film is pierced, such as when it is sutured in place. Integrated or incorporated wireless device and/or sensor would be to track certain patient environmental or physical conditions, wherein said sensor would then relay patient related information wirelessly when a receiver or recorder is placed on or near the implant and/or patient.

In some embodiments, the present invention provides articles of manufacture comprising, consisting of, or consisting essentially of: a polymer film and/or coating (e.g., which is transparent) with a top surface and a bottom surface, wherein the polymer film comprises, consists of, or consists essentially of, a para-xylene polymer, wherein the polymer film has a thickness between 1 μm and 5 mm (e.g., 1 . . . 5 . . . 15 . . . 25 . . . 38 . . . 55 . . . 75 μm . . . 1 mm . . . 3 mm . . . 5 mm), wherein the top surface has a water contact angle between 75 and 95 degrees (e.g., 75 . . . 79 . . . 81 . . . 84 . . . 88 . . . 91 . . . or 95 degrees), and/or a surface roughness of 1.0 nm and 10.0 nm (e.g. 1.0 . . . 3.0 . . . 5.0 . . . or 10.0 nm), and/or a Carbon (C) to Oxygen (O) ratio of 2:1 and 18:1 (e.g., 2:1 ... 6:1 ... 10:1 ... 14:1 ... 18:1) to create anti-adherent surfaces, wherein the polymer film and/or coating is sized to serve as a tissue separator and/or adhesion barrier in a subject. For adherent surfaces, a water contact angle between 1-75 degrees may be employed (e.g., 1 ... 15 ... 30 ... 45 ... 60 ... 75) and C to O ratios less than 2:1 which may include the presence of carbonyl, carboxyl, and nitrogen containing groups to create adherent surfaces wherein the polymer film and/or coating is sized to serve as a tissue separator, tissue adherent platform and/or adhesion barrier in a subject. In certain embodiments, the polymer film has an optical transmission of 60-99.9% in the high visible (400-1000 nm) and near infra-red (3200-6000 cm) range.

In certain embodiments, the present invention provides methods for separating areas in an internal region of a subject comprising: inserting an article of manufacture into an internal region of a subject between first and second areas, wherein the article of manufacture consists of, or consists essentially of, a polymer film and/or coating with a top surface and a bottom surface, wherein the polymer film comprises, consists of, or consists essentially of, a para-xylene polymers, wherein the polymer film and/or coating has a thickness between 1 μm and 5 mm (e.g., 1 ... 5 ... 15 ... 25 ... 38 ... 55 ... 75 μm ... 1 mm ... 5 mm), and wherein the top surface has a water contact angle between 75 and 95 degrees (e.g., 75 ... 79 ... 81 ... 84 ... 88 ... 91 ... or 95 degrees). In certain embodiments, the polymer film is contained and/or inserted into or within a Teflon flap/envelope or other component acting to hold said polymer film in place, this combination of materials, in certain embodiments, is further contained or inserted into a final secondary packaging, which is sealed and then sterilized.

In certain embodiments, provided herein are the creation of individual or multiple adherence points, or a completely adherent side, to said para-xylene films and/or coatings. The function of these points would be to adhere cellular tissue and/or organ surfaces to a point, portion, or side of the para-xylene film. The number, size, and extent of these adherence points would be dependent on the application. In particular embodiments, these areas would also be limited in scope or size such that they are sufficient to facilitate film adherence or attachment in a permanent manner to one portion or side of a tissue/organ surface or body cavity lining.

In particular embodiments, manufacture of said adherence points, areas, or side would be through some method of oxidation, oxygen plasma etching, ambient air plasma etching, and/or exposure, or UV irradiation, or any combination thereof which would impart primarily carbonyl functional groups, potentially carboxyl groups, or groups containing nitrogen, the predominate species being carbonyl groups. This oxidative functionalization would result in water contact angles of 1-75 and a total carbon to oxygen ratio of less than 2:1.

In certain embodiments, the adherence points would only be imposed upon one side of the para-xylene film. In other embodiments, the adherence points are present on both sides of the film. In some embodiments, the function of the adherence points would be for the integration or immobilization of the para-xylene film to the cellular tissue and/or organ surface or body lining in lieu of using permanent sutures, staples, or some other form of immobilization. Thus, creating an adherent side (oxidized) and non-adherent para-xylene film which would serve as a tissue separator and/or adhesion barrier preventing interaction to said non-adherent side/portion while being anchored (e.g., solely) by adherent points on opposing side.

In certain embodiments, implantation of an adherent/non-adherent film can be deployed as a means of ensuring proper wound closure of the integument (skin), muscle and/or musculature, sub-cutaneous tissue, and/or connective tissue so as to not incur incisional hernias, prevention of incisional hernia after a surgical procedure. Whereas the adherent side (anterior) of the para-xylene film would be affixed to the parietal side of the body cavity and the non-adherent (posterior) side would face the visceral side, preventing significant interaction between the tissue and organ surfaces decreasing the likelihood of surgical adhesions to or around the incision site.

In certain embodiments implantation of adherent/non-adherent film could be deployed in an effort to separate individual organ surfaces from one another or separate adherence of visceral portions of the peritoneum from parietal portions of the body cavities. Placement of an adherent/non-adherent film would be to separate organs from one another, due to the confining nature of the surgical procedure, such para-xylene films could be placed between individual organs or folds within the intestines, preventing bowel obstruction, or organ to organ adherence. This situation would present itself, for example, when suturing or other methods of permanent immobilization cannot be employed due to the lack of space and/or nature of the procedure. In certain embodiments, the para-xylene films or meshes described herein are used as a trans-vaginal support, lift, separator, and/or assist in pelvic organ prolapse, or support, lift, and/or separate any other form of organ related prolapse which may occur.

In certain embodiments, application of para-xylene film implanted in a subject (e.g., in a temporary fashion) further comprises a tether. In certain embodiments, the tether is composed of a strand, or elongated para-xylene strip originating from the center, end, or some point of the film surface and/or edge of said para-xylene film, which upon implantation the tether/strip would traverse the internal areas of implantation and protrude externally through the integument (skin), muscle and/or musculature, sub-cutaneous tissue, and/or connective tissue at the incision site. Said tether, protruding from the wound site and/or surgical incision point may, for example, be bandaged over to assure risk of infection is minimized. The presence of the tether and/or strip would allow for complete removal of para-xylene film after a period determined by a clinician, surgeon etc. Inability of cells and tissue to adhere or interact with the film would permit the tether/strip to prevent full wound closure at the site of incision specifically where the tether/strip protrudes from the incision site, allowing for removal of the para-xylene film after any number of days following the surgical procedure. Immobilization of said tethered para-xylene film, the securing of the main internal portion of the film, could be done using degradable sutures or similar resorbable means. Upon degradation of resorbable fixation, the film could/would be safely removed. Manufacturing of temporary para-xylene films with integrated tether/strip could be manufactured, for example, as one piece.

In certain embodiments, deposition of a para-xylene polymer onto the outer surface of a surgical implant that is permanent, non-resorbable, non-degradable mesh or other related permanent implant, is in a manner that said polymer uniformly coats the mesh or implant. In particular embodiments, each side of the mesh or implant may be characterized by a visceral side (e.g., typically posterior orientation) and a parietal side (e.g., typically anterior orientation). In certain embodiments, composition of the top surface (bottom surface would adherent to mesh or device) where anterior surface is tuned through some method of oxidation (e.g., plasma oxidation and/or UV irradiation) such that the anterior surface acts to integrate or promote tissue adherence or attachment, while the non-oxidized posterior surface prevents such cell/tissue interaction or attachment. Thus, the tuning of the surface will promote device integration while the opposing side would prevent such interaction to body tissues or organ surfaces either adjacent or those which come into contact with said device. In particular embodiments, this would be especially important for implanted devices within various body cavities whereby a surface which could promote integration on one surface, while preventing or repel tissue attachment to the body cavity or adjacent organ(s) further aiding in preventing adhesions or scar formation to the opposing or opposite non-oxidized surface.

In certain embodiments, the purpose of said coating would be to prevent, resist, and/or repel tissue and/or organ adhesion and/or integration of said implant into the surrounding tissue surfaces and/or organ surfaces, specifically interaction with the visceral peritoneum or the visceral side, side facing or interacting with the organ surface(s) most likely posterior. This portion of most traditional mesh designs is composed of a smooth, or less rough side, characterized by a smooth web, netting, or interweaving of mesh strands created to present a smooth surface meant to face, or come into contact with the visceral peritoneum and/or visceral organ surfaces. In certain embodiments, such surgical mesh designs may or may not be composed of parylene as described herein.

In additional embodiments, the parylene film will act (e.g., alone) as a hernia mesh material, or wound closure mesh/material. In certain embodiments, the parylene film possesses perforations, holes, and/or cut-outs (e.g., placed strategically across the film giving the appearance of a mesh, net, and/or webbing). Such an embodiment is shown in FIG. 8. In particular embodiments, the perforations, holes, or cut-out portions within the film allow flexibility and stretching in order to accommodate the flexing and stretching of integument (skin), muscle and/or musculature, sub-cutaneous, and/or connective tissue when the film is implanted. In particular embodiments, the parylene mesh, net, or webbing will have thickness measurements between 1 µm to 5 mm. The thickness of said parylene film will facilitate the strength and flexibility required for a device implanted in such a manner.

In certain embodiments, the para-xylene coating of the parietal facing portion of the surgical mesh is characterized by a rough web, netting, or interweaving of mesh strands creating varying topography such as to maximize mesh integration into the parietal peritoneum or parietal surface most likely anterior. The mesh design may or may not be composed of para-xylene as described herein. In certain embodiments, the peritoneal side may be treated to elicit and/or promote interaction, adherence to this surface/side. Oxidation of only this portion or side of coating/device (anterior) would create adherence, through any means of oxidation, oxygen plasma etching, etc. In certain embodiments, steps could be taken, such as through immersing or shielding of the visceral portion, through use of a Polydimethylsiloxane (PDMS) stamp or other material, which could sufficiently prevent oxidation of the visceral side, allowing for oxidation of the parietal surface alone and subsequent alteration to surface chemistry resulting in a carbon to oxygen content ratios of less than 2:1, contain predominately carbonyl groups, a lesser degree carboxyl groups, but also potentially contain a range of nitrogen groups resulting in water contact angles 1-75, attributed to oxidized para-xylene physical and chemical characteristics, excluding surface roughness which would be determined by the surface of said mesh.

In particular embodiments, the internal region of the subject is selected from the group consisting of: dorsal cavity, ventral cavity, thoracic cavity, pleural cavity, mediastinum, abdominopelvic cavity, abdominal cavity, pelvic cavity, lumbar region, umbilical region, inguinal region, hypogastric region, abdominal region, peritoneal surfaces, visceral surfaces, mesothelial surfaces, antebrachial, axillary, brachial, buccal, carpal, cervical, coxal, crural, cubital, femoral, mental region, orbital region, patellar region, pubic region, tarsal region, thoracic cavity, gluteal region, lumbar region, occipital region, popliteal region, scapular region, sural region, nasal region, cephalic region, oral cavity, otic region, acromial region, deltoid region, digital area, sternal region, pectoral region, mammary region, pedal region, plantar region, calcaneal region, sacral region, vertebral region, sagittal region, coronal region, transverse region, oblique region, brain, spinal cord, heart, right lung, left lung, right kidney, left kidney, and bladder. In other embodiments, the first area comprises the heart and the second area comprises the sternum.

In some embodiments, the present invention provides system comprising: a) an article of manufacture consisting of, or consisting essentially of: a polymer film and/or coating with a top surface and a bottom surface, wherein the polymer film consists of, or consists essentially of, a para-xylene polymer(s), wherein the polymer film and/or coating has a thickness between 1 µm and 75 µm (e.g., 1 . . . 5 . . . 15 . . . 25 . . . 38 . . . 55 . . . or 75 µm), wherein the top surface has a water contact angle between 75 and 95 degrees (e.g., 75 . . . 79 . . . 81 . . . 84 . . . 88 . . . 91 . . . or 95 degrees), and wherein the polymer film is sized to serve as a tissue separator, tissue adherent platform, and/or adhesion barrier in a subject; and b) a packaging component, wherein the article of manufacture is located inside the packaging component. In certain embodiments, the article of manufacture is sealed inside the packaging component such that the article of manufacture remains sterile while inside the packaging component.

In further embodiments, the present invention provides articles of manufacture comprising: a) a device comprising at least one surface, and b) a polymer film coating at least a portion of the at least one surface of the device (e.g., medical device), wherein the polymer film has an exposed top surface, wherein the polymer film consists of, or consists essentially of, a para-xylene polymer (s), wherein the polymer film has a thickness between 1 µm and 75 µm, and wherein the top surface has a water contact angle between 75 and 95 degrees. In certain embodiments, the device is a medical device selected from the group consisting of: a catheter, a hernia mesh, a stent, an implantable cardioverter defibrillators (ICD), a balloon dilator, a band ligator, a surgical clip, forceps, a surgical guidewire, a surgical snare, and an implantable pulse generator.

In particular embodiments, the polymer film is sterilized. In other embodiments, the para-xylene polymer comprises parylene C. In further embodiments, the para-xylene polymer is selected from the group consisting of: parylene A, parylene AM, parylene AF4, parylene SF, parylene HT, parylene X, parylene N, and parylene D. In additional embodiments, the article of manufacture consists of the polymer film and/or coating. In other embodiments, the subject is a human, cat, dog, horse, cow, pig, or other domesticated animal.

In certain embodiments, the water contact angle for the top surface is between 80 and 90 degrees (e.g., about 80, 81, 82, 83, 84, 85, 86, 87, 88, 89, or 90 degrees). In further embodiments, the bottom surface has a water contact angle between 75 and 95 degrees (e.g., 75 . . . 79 . . . 81 . . . 84 . . . 88 . . . 91 . . . or 95 degrees). In other embodiments, the bottom surface has a water contact angle of 1-75 degrees (e.g., 75 . . . 79 . . . 81 . . . 84 . . . 88 . . . 91 . . . or 95 degrees) or 96-180 degrees (e.g., 96 . . . 110 . . . 120 . . . 150 . . . or 180). In certain embodiments, the bottom surface is oxidized. In some embodiments, the polymer film has a thickness between 5 µm and 25 µm (e.g., 5 . . . 10 . . . 15 . . . 20 . . . or 25 µm). In further embodiments, the top surface has a RMS roughness between 1.0 nm and 10.0 nm (e.g., 2.5 . . . 3.5 . . . 5.0 . . . 6.5 . . . or 7.5 nm). In additional embodiments, the bottom surface has a RMS roughness between 1.0 nm and 10.0 nm (e.g., 2.5 . . . 3.5 . . . 5.0 . . . 6.5 . . . or 7.5 nm). In other embodiments the film has an optical transmission of 60-99.9% in the high visible (400-1000 nm) and near infra-red (3200-6000 cm) range.

In some embodiments, the present invention provides compound films. For example, in certain embodiments, the present invention provides articles of manufacture comprising, consisting essentially of, or consisting of: a compound film, wherein the compound film comprises, consists essentially of, or consists of: a) a base polymer film with a base top surface and a base bottom surface, wherein the base polymer film comprises a first para-xylene polymer and has a thickness between 1 µm and 75 µm (e.g., 1 . . . 5 . . . 15 . . . 25 . . . 38 . . . 55 . . . or 75 µm); b) a first therapeutic molecule layer disposed on the base top surface, wherein the first therapeutic molecule layer comprises first therapeutic molecules; and c) a first cover polymer film with a first cover top surface and first cover bottom surface, wherein the first cover bottom surface covers the first therapeutic molecule layer, and wherein the first cover polymer film comprises a second para-xylene polymer and has: i) an elution-allowing (sub-conformal) thickness between about 150 nm and 600 nm (e.g., 150 . . . 250 . . . 350 . . . 450 . . . 550 . . . and 600 nm) mediating passive transport of the therapeutic(s) across said polymer film cover, or ii) a non-elution allowing (conformal) thickness between about 1 µm and 75 µm (e.g., 1 . . . 5 . . . 15 . . . 25 . . . 38 . . . 55 . . . or 75 µm).

In certain embodiments, the present invention provides methods for separating areas in an internal region of a subject (and/or treating inflammation or atrial fibrillation) comprising: inserting an article of manufacture as described herein (e.g., containing a compound film) into an internal region of a subject between first and second areas. In particular embodiments, the internal region of the subject is selected from the group consisting of: dorsal cavity, ventral cavity, thoracic cavity, pleural cavity, mediastinum, abdominopelvic cavity, abdominal cavity, pelvic cavity, lumbar region, umbilical region, inguinal region, hypogastric region, abdominal region, peritoneal surfaces, visceral surfaces, mesothelial surfaces, antebrachial, axillary, brachial, buccal, carpal, cervical, coxal, crural, cubital, femoral, mental region, orbital region, patellar region, pubic region, tarsal region, thoracic cavity, gluteal region, lumbar region, occipital region, popliteal region, scapular region, sural region, nasal region, cephalic region, oral cavity, otic region, acromial region, deltoid region, digital area, sternal region, pectoral region, mammary region, pedal region, plantar region, calcaneal region, sacral region, vertebral region, sagittal region, coronal region, transverse region, oblique region, brain, spinal cord, heart, right lung, left lung, right kidney, left kidney, and bladder. In certain embodiments, the first area comprises the heart and the second area comprises the sternum. In additional embodiments, the first or second cover polymer film has an elution-allowing thickness between 150 nm and 600 nm (e.g., 150 . . . 250 . . . 350 . . . 450 . . . 550 . . . and 600 nm) mediating passive transport of the therapeutic(s) across said polymer film cover, and wherein the first and/or second therapeutic molecules pass out of the compound film into the internal region of the subject. In other embodiments, the first or second cover polymer film has a non-elution allowing thickness between 1 µm and 75 µm (e.g., 1 . . . 5 . . . 15 . . . 25 . . . 38 . . . 55 . . . or 75 µm), and wherein the method further comprises suturing the compound film in the internal region in the subject, wherein the suturing generates holes in the compound film that allow the first and/or second therapeutic molecules to pass out of the compound film into the internal region of the subject.

In certain embodiments, the present invention provides systems comprising: a) an article of manufacture as described herein (e.g., with a compound film); and b) a packaging component, wherein the article of manufacture is located inside the packaging component. In particular embodiments, the article of manufacture is sealed inside the packaging component such that the article of manufacture remains sterile while inside the packaging component. In other embodiments, the compound film has a thickness (i.e., total thickness) between about 1 µm and 75 µm. In other embodiments, the article of manufacture further comprises a device, wherein at least a portion of the device is coated with the compound film. In additional embodiments, the device comprises a medical device.

In further embodiments, the first cover top surface is an outermost layer of the compound film and has a water contact angle between 75 and 95 degrees. In other embodiments, the compound film further comprises: d) a second therapeutic molecule layer (and optionally a third, fourth, fifth, sixth, etc. therapeutic molecule layer) disposed on the first cover top surface (and disposed on the next available outer surface for the third, forth, fifth, sixth, etc. therapeutic molecule layers), wherein the second therapeutic molecule layer comprises second therapeutic molecules (and the additional layers comprise third, fourth, fifth, etc. therapeutic molecule layers). In some embodiments, the compound film further comprises: e) a second cover polymer film with a second cover top surface and a second cover bottom surface, wherein the second cover bottom surface covers the second therapeutic molecule layer, and wherein the second cover polymer film comprises a third para-xylene polymer and has: i) an elution-allowing thickness between about 150 nm and 600 nm, or ii) a non-elution allowing thickness between about 1 µm and 75 µm.

In particular embodiments, the second cover top surface is an outermost layer of the compound film and has a water contact angle between 75 and 95 degrees. In further embodiments, the article of manufacture consists of, or consists essentially of, the compound film, and wherein the compound film is sized to serve as a tissue separator and/or adhesion barrier in a subject. In other embodiments, the base bottom surface is an outermost layer of the compound film and has a water contact angle between 75 and 95 degrees.

In other embodiments, the compound film further comprises: d) a second therapeutic molecule layer disposed on the base bottom surface, wherein the second therapeutic molecule layer comprises second therapeutic molecules. In other embodiments, the compound film further comprises: e) a second cover polymer film with a second cover top surface and a second cover bottom surface, wherein the second cover bottom surface covers the second therapeutic molecule layer, and wherein the second cover polymer film comprises a third para-xylene polymer and has: i) an elution-allowing thickness between about 150 nm and 600 nm, or ii) a non-elution allowing thickness between about 1 µm and 75 µm or 1 um and 5 mm.

In certain embodiments, in lieu of a therapeutic being deposited or integrated between 2 conformal or encapsulating layers or para-xylene, the integration of a wireless device/sensor is employed. This wireless device or sensor could be used, for example, to track certain patient environmental or physical conditions, where said sensor would then relay patient related information wirelessly when a receiver or recorder is placed on or near the implant and/or patient. The sensor would be sandwiched or encapsulated between para-xylene layers. Manufacture of the sensor could be achieved by a single thinner deposition of para-xylene, placing or laying of the wireless device or sensor and then depositing another thicker layer on top of the initial para-xylene layer and device. Resultant device would be a thin base layer and then a significantly thicker second layer bonding or sealing device between two layers of para-xylene with a device or sensor in the middle between the top or bottom surface.

In certain embodiments, the compound film is sterilized. In further embodiments, the first and/or second para-xylene polymer comprises parylene C. In other embodiments, the first and/or second (and/or third, fourth, etc.) para-xylene polymer is selected from the group consisting of: parylene A, parylene AM, parylene AF4, parylene SF, parylene HT, parylene X, parylene N, and parylene D. In some embodiments, the base top surface is oxidized. In additional embodiments, the base polymer film has a thickness between 5 μm and 25 μm (e.g., 5 . . . 10 . . . 15 . . . 20 . . . or 25 μm). In additional embodiments, the first cover top surface has a RMS roughness between 1.0 nm and 10.0 nm (e.g., 2.5 . . . 3.3 . . . 4.1 . . . 6.3 . . . or 7.5 nm). In other embodiments, the base bottom surface has a RMS roughness between 1.0 nm and 10.0 nm (e.g., 2.5 . . . 3.3 . . . 4.1 . . . 6.3 . . . or 7.5 nm). In further embodiments, the film has, an optical transmission of 60-99.9% in the high visible (400-1000 nm) and near infrared (3200-6000 cm) range.

In certain embodiments, the size and shape of the film will take a variety of forms. This includes square to rectangular forms with rounded edges (e.g., 2"×3", 3"×3" 3"×4", 5"×6", 6"×6", 6"×7" inches, etc) thereby revealing a shape with no sharp corners and/or edges. In further embodiments the shape will take a circular (e.g., as shown in FIG. 7), oval, or ovoid shapes or form (e.g., 2", 3", 4" 5" inch diameters, etc). Other embodiments may take the form of a triangular shape, possessing rounded edges (e.g., 2", 3", 4" 5" inch heights, etc.). In additional embodiments, the film will be provided in a larger single piece (e.g., 9"×9", 9"×10", 10"×11" inches, etc) where the end user, surgeon, and/or clinician will cut the film to shape according to procedure and/or application, or intended use. In other embodiments, the film will have a clover leaf, or club shape or appearance to include a two, three, or four leaf clover/club type design to facilitate the wrapping or ability to conform to spherical or three dimensional shaped objects such as various body organs and/or body cavities without excessive bunching, wrinkling or crimpling along certain edges or portions of said film.

DETAILED DESCRIPTION

Figure 1:
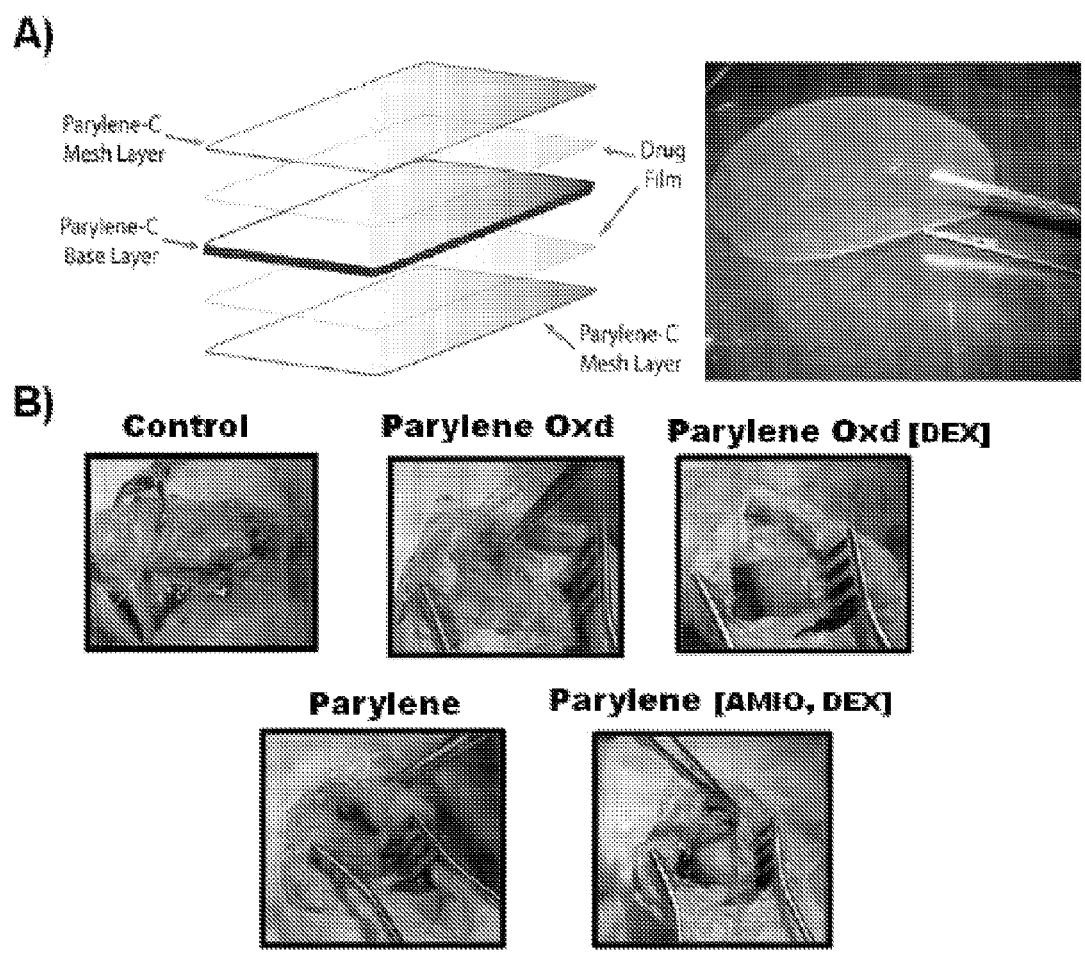
FIG. 1: A) Schematic representation of an exemplary stand alone Parylene-C (PPX) derived Drug Delivery Platform (DDP) (e.g., for implantation to reduce incidence of perioperative inflammation and postoperative atrial fibrillation). The transparency and thin profile of the film are physical properties lending to the amenable nature of the device. Integration of therapeutics, such as Dexamethsaone (DEX) and Amiodarone (AMIO), into the PPX film increases the effectiveness with which the device can counteract complications stemming from surgery (e.g., cardiovascular surgery). B) Postoperative images taken at the time of repeat sternotomy showing film involvement among the experimental conditions as described in Example 1 below.

The present invention provides single sheet and compound para-xylene films for therapeutic uses. For example, the present invention provides single sheet para-xylene films useful as tissue separators and/or adhesion barriers in a subject, where the top and/or bottom surfaces of such films have a water contact angle between 75 and 95 degrees (e.g., to prevent adhesion formation). The present invention also provides compound films composed of at least two para-xylene polymer films with a therapeutic molecule layer in between. Such compound films, when used in vivo (e.g., as a tissue separator and to treat inflammation or atrial fibrillation) allow either therapeutic molecule elution through one of the paraxylene layers, or therapeutic molecule release when the compound film is pierced, such as when it is sutured in place.

The present invention is not limited by the size of the single sheet and compound films. Preferably, these films are sized to fit inside a subject to serve as a tissue separator and/or adhesion barrier. In certain embodiments, the films are 18×13.5 cm; or 9×9 cm; or 10×10; or 20×7 cm. In certain embodiments, the surface area of the films is about 200 cm$^2$; or between 10 and 400 cm$^2$ (e.g., 10 . . . 30 . . . 75 . . . 140 . . . 243 . . . 333 . . . 380 . . . or 400 cm$^2$). The present invention is not limited by the shape of the films. Exemplary shapes include circles, ovals, squares, octagons, etc.

The present invention is not limited by the type of therapeutic molecules that can be included in the compound films. Therapeutic molecules include, but are not limited to, any type of biologics, dexamethasone, amiodarone, biosimilars, thrombin inhibitors, antithrombogenic agents, thrombolytic agents, fibrinolytic agents, vasospasm inhibitors, calcium channel blockers, vasodilators, antihypertensive agents, antimicrobial agents, antibiotics, inhibitors of surface glycoprotein receptors, antiplatelet agents, antimitotics, microtubule inhibitors, anti secretory agents, actin inhibitors, remodeling inhibitors, antisense nucleotides, anti metabolites, antiproliferatives, anticancer chemotherapeutic agents, anti-inflammatory steroid or non-steroidal anti-inflammatory agents, immunosuppressive agents, growth hormone antagonists, growth factors, dopamine agonists, radiotherapeutic agents, extracellular matrix components, inhibitors, free radical scavengers, chelators, antioxidants, anti polymerases, antiviral agents, photodynamic therapy agents, gene therapy agents; small molecules, proteins, multiprotein macromolecules (e.g., antibodies), nucleic acids (including, but not limited to, siRNA, shRNA, miRNA, etc.); hydrophilic small molecule drugs, hydrophobic small molecule drugs, steroidal small molecule drugs, macrocyclic small molecule drugs, small molecule drugs without bulky side groups, small molecule drugs with bulky side groups, small molecule drugs in pharmaceutical acceptable salt forms, peptide biologics, protein biologics, multi-chain protein biologics, glycosylated protein biologics, immunoglobulins, micro chain nucleic acid biologics, short chain nucleic acid biologics, nucleic acid biologics, aptamer biologics, protein-nucleic acid complex biologics, lipid biologics, lyposome biologics and PEGylated forms of any of the foregoing, dexamethasone, doxorubicin, IgG, interferon2b, mitomycin, clopidogrel, paclitaxel, hormones, hormone mimetics and hormone derivatives, including plant hormones.

In certain embodiments, the films of the present invention are provided in a system or kit along with a packaging component (e.g., container for the films when they are stand alone components for tissue separation or adhesion barriers). In certain embodiments, the packaging component is sized to fit the film and is a foil lined bag commonly used for medical devices, such as adhesion barriers. In particular embodiments, the packaging component is a gas-impermeable, foil bag. In some embodiments, the packaging component further includes written instructions for proper care and/or use of the films.

The present invention is not limited by the fabrication technique used to make the films of the present invention. For example, the films can be fabricated upon a solid surface as a temporary platform which can be eventually removed for standalone activity. This solid surface can be, for example, a glass slide, coverslip, silicon wafer, plastic disc and the like. In certain embodiments, the films can be generated as follows. Onto to a solid surface, a base layer of para-xylylene polymer is deposited. This can be done, for example, via a room temperature chemical vapor deposition process. In the chemical vapor deposition process, the para-xylene monomer is sprayed as a monolayer onto the solid surface such that the monomer reversibly attaches to the solid surface and self polymerizes. The result being a film of para-xylylene is created by deposition onto the solid surface. In certain embodiments, a Specialty Coating Systems Lab Coater, per the manufacturer's protocol, can be used to deposit a base layer of pary-xylene (e.g., parylene C) onto a glass disc via a room temperature chemical vapor deposition.

The surface of the films of the present invention, in some embodiments, may be oxidized. Oxidative functionalization may be accomplished, for example, by ultraviolet light, a plasma cleaner, chemically driven oxidization or any other oxidation processing of the para-xylene.

In certain embodiments, a layer of therapeutic molecules is deposited onto a surface of the films of the present invention. The therapeutic may be, for example, physically, ionically, or covalently linked to the surface of the layer. An exemplary method to dispose about, permeate and/or deposit the therapeutic on or to a layer is a spotting followed by evaporation. In this method, a solvent containing the therapeutic is deposited on the layer. The solvent then evaporates off slowly. As solvent evaporates off, the therapeutic falls down and depending upon the wettability of the layer, the deposited therapeutic diffuses in the layer. This leaves a dry therapeutic that is permeated in and/or disposed about the surface of the layer and forms a reservoir of therapeutic.

In certain embodiments, a plurality of distinct laminated layers or multilayer can be deposited by repeating the above process. In subsequent chemical vapor depositions, the para-xylene monomer is sprayed onto an underlying layer of polymerized para-xylylene. Similar to when the monomer is sprayed on the solid surface, it self polymerizes. Unlike when the monomer is sprayed on the solid surface, when sprayed on an underlying layer of polymerized para-xylylene, it essentially irreversibly attaches to form a laminate. This process is repeated as many times to build up the number of desired layers. In between repeating the deposition process, an oxidative functionalization process can be performed.

EXAMPLES

Example 1

Para-Xylene Polymer Films for Adhesion Prevention and Reduction in Inflammation

This Example describes the construction and use of para-xylene polymer films to prevent adhesions and inflammation in vivo.

Suppression of both perioperative inflammation and post-operative atrial fibrillation has been hindered due to an absence of effective drug delivery platforms (DDP) in the post-operative cardiac setting. Localized released of an anti-inflammatory and anti-arrhythmic agents may be more effective than intravenous drug delivery in order to improve patient outcomes. An investigation utilizing a Parylene-C nanostructured therapeutic film infused with dexamethasone (DEX) and amiodarone (AMIO) to inhibit inflammation and atrial fibrillation was performed as described below.

A Parylene-C (PPX) film was tested in an established rabbit model of pericardial adhesion formation. Following sternotomy, the anterior pericardium was resected and the epicardium was abraded. Rabbits were randomly assigned to five treatment groups: Control (plasma oxidized polystyrene), oxidized PPX (PPX-Oxd), PPX-Oxd infused with DEX (PPX-Oxd[DEX]), native PPX (PPX), and PPX infused with DEX and AMIO (PPX[AMIO, DEX]). After 4 weeks post-sternotomy, pericardial adhesions were evaluated for gross adhesions using an established 4-point grading system, histological evaluation for neotissue fibrosis (NTF) on the epicardium. Atrial fibrillation duration and time per induction were measured.

The PPX[AMIO, DEX] group had a significant reduction in mean adhesion score compared with the Control group (Control 2.75±0.42 vs. PPX[AMIO, DEX] 0.25±0.42) ($P<0.01$). The PPX[AMIO. DEX] group was similar to native PPX (PPX 0.38±0.48 vs. PPX[AMIO, DEX] 0.25±0.42) (P=NS). Adhesions in the PPX-Oxd group were not distinguishable from the Control group (PPX-Oxd 2.83±0.41 vs Control 2.75±0.42) (P=NS). A reduction in neotissue fibrosis was present in the PPX[AMIO, DEX] group compared to the Control group (PPX[AMIO, DEX] 0.80±0.10 mm vs. Control 1.78±0.13 mm)($P<0.001$). Total duration of atrial fibrillation was decreased in rabbits with PPX[AMIO, DEX] films compared to Control (9.5±6.8 sec vs. 187.6±174.7 sec, p=0.003). Time of atrial fibrillation per successful induction decreased among PPX[AMIO, DEX] films compared to Control (2.8±1.2 sec vs. 103.2±178 sec, p=0.004).

These results indicated that DEX and AMIO impregnated Parylene-C films are associated with reduced perioperative inflammation and a diminished duration of atrial fibrillation. Epicardial application of AMIO, DEX films is a useful strategy to prevent post-operative cardiac complications.

Materials and Methods

Material Fabrication 20 grams of Parylene-C (dichloro(2,2)paracyclophane) (PPX) (Paratech Coating Inc., Aliso Viejo, Calif.) was deposited onto SSP Type 110 silicon wafers (University Wafer, Boston, Mass.). Deposition occurred within a Labcoter 2 PDS 2010 (Specialty Coating Systems SCS, Indianapolis, Ind.) under default conditions.[13] Drug loading involved applying 150 µg of DEX (Alfa Aesar, Ward Hill, Mass.) and 800 µg of AMIO (U.S. Pharmacopeia, Rockville, Md.) on PPX surfaces (600 µg of DEX and 3.2 mg of AMIO total). Following drug loading, a 0.4 gram sub-conformal PPX layer was deposited on the drug layer followed by plasma oxidation of the surface.

A second drug layer was then applied, and a second 0.4 gram sub-conformal PPX was deposited on top of the drug layer. This last layer was not oxidized and instead was left hydrophobic. Sterilization of drug loaded films was completed through exposure to ethylene oxide gas utilizing an Anprolene AN74i gas sterilizer (Anderson Products, Inc. Haw River, N.C.) per manufacturer's recommendations.

In-vitro Analysis

In-vitro analysis and drug release was completed through deposition of PPX on varying culture plates. Surface treatment of prepared PPX culture plates either had plasma oxidation (Oxd) or lack thereof resulting in hydrophilic or hydrophobic surfaces (native form). RAW264.7 macrophages and NIH-3T3 fibroblasts were analyzed on varying surfaces to determine in-vitro response. Cells were kept in DMEM media supplemented with 10% FBS and 1% Pen/Strep in humidified atmosphere with 5% $CO^2$. Cellular analysis was completed through the application of time lapse bright field imaging in addition to multiple cellular assays examining viability (MTT, Roche Diagnostics), proliferation (CyQUANT, Life Technologies) and adhesion (Vybrant, Molecular Probes) onto polystyrene, representing baseline biocompatible control surfaces, and various PPX surfaces. RNA isolation was accomplished utilizing TRIzol reagent (Invitrogen Corporation, Carlsbad, Calif.) per the manufacturer's guidelines. cDNA was synthesized using the iScript Select cDNA Synthesis Kit (Quanta Biosciences, Gaithersburg, Md.). PCR was done using SYBER Green detection reagents (Quanta Biosciences, Gaithersburg, Md.) and appropriate primers for IL-6 and β-Actin (Integrated DNA Technologies, Coralville, Iowa). Samples were amplified using a MyiQ real-time PCR detection system (Bio-Rad).

Material Characterization

X-ray Photoelectron Spectroscopy (XPS) was completed using an Omicron ESCA probe (Omicron NanoTechnology, Eden Prairie, Minn.) coupled with an EA125 hemispherical energy analyzer. Photoemission was stimulated through monochromated Al (KR) radiation (1486.6 eV) with a power output of 300 W under ultra-high vacuum (UHV). Survey scans completed by the analyzer were maintained in constant analyzer energy (CAE) mode at 50 eV. Binding energies were referenced at the C 1s (285.0 eV) binding energy set. The binding energy spectrum for each XPS survey scan ranged from 0-1200 eV. Surface wettability was determined through static contact angle measurements using a VCA Optima contact angle goniometer (AST Products, Inc., Billerica, Mass.) equipped with an automated pipetting system. Ultrapure $H_2O$ volumes of 15 μl were dispensed on varying substrates and subsequent images and angle measurements were collected through AutoFAST Imaging and SPC software respectively. Angle measurements were collected in air and under ambient temperatures. Atomic Force Microscopy (AFM) images were collected utilizing a CP Research (Formally ThermoMicroscopes now Veeco Instruments Inc., Plainview N.Y.) AFM. Imaging was performed in intermittent contact mode using a Si probe, (μMasch, NSC36A) with a nominal tip radius curvature of 10 nm. All measurements occurred under atmospheric conditions and ambient temperatures. AFM images were rendered and analyzed using WSXM SPM analysis software.[14] Profile measurements concerning film thickness were completed utilizing a Veeco Dektak 150 Surface Profiler (Veeco Instruments Inc., Plainview, N.Y.) using a standard scan option equipped with a 2.5 μm stylus with an applied force of 5.0 mg. Scan length and duration were confined between 1500-2000 μm and 90 seconds respectively, resulting in horizontal resolutions of 0.055 μm to 0.075 μm and vertical resolution maximum of 524 μm. All measurements were completed in air and under ambient conditions. Analysis was completed using Dektak V9 Software. Attenuated total reflection (ATR) Fourier transform infrared (FT-IR) spectroscopy was performed utilizing a Thermo Nicolet Nexus 870 IR Spectrophotometer (ThermoFisher Scientific Inc., Waltham, Mass.). FT-IR analyses of the films under investigation were loaded onto an attenuated reflectance kit (ARK) with a Zinc Selenium (ZnSe) crystal contained within a N2 purged chamber. A liquid nitrogen cooled mercury cadmium telluride (MCT) detector completed 64 scans with a resolution of 8 $cm^{-1}$ over a range of 4,000-650 $cm^{-1}$ at room temperature. Samples were loaded onto the ZnSe crystal at a point to point contact interface under maximum allowable load/pressure. ATR and further baseline corrections were completed utilizing Omnic and eFTIR software.

Animal Preparation

Thirty New Zealand white female rabbits (4 kg) were randomly assigned to one of five groups: Control group (N=6), oxidized PPX (PPX-Oxd, N=6), PPX-Oxd infused with DEX (PPX-Oxd[DEX],N=6), native PPX (PPX, N=4), and PPX infused with DEX and AMIO (PPX[AMIO, DEX], N=6). Initial sedation with acepromazine (0.5 mg/kg subcutaneous) was followed by general anesthesia induction using ketamine (40 mg/kg) and xylazine (7 mg/kg). Endotracheal intubation was achieved with a 3- or 4-mm tube and anesthesia was maintained intraoperatively with 1.5-2.5% isoflurane. An intravenous catheter was placed in the marginal ear vein. Cardiorespiratory monitoring was maintained throughout surgery.

Rabbit Pericardiotomy Model

Following clipping of the fur at the operative site, the skin was prepped with betadine. Approach through a midline sternotomy allowed complete anterior pericardiotomy to be made between the left and right phrenic nerves. To incite microvascular bleeding and pericardial adhesion formation, a gauze pad was used to abrade the epicardial surface of the pericardium for 5 minutes. Experimental biologic membranes were fixed to the edges of the pericardium using four 5.0 polypropylene sutures. Control animals had 4 sutures placed in the open pericardium but no membrane. Tube thoracostomy was employed during closure of the sternotomy and subsequently removed.

Arrhythmia Induction and Measurement

Defibrillation patches were placed on the lateral aspect of the thorax to provide defibrillation if required and to produce a single-lead surface electrocardiogram. The electrocardiogram was recorded using a Medtronic LIFEPAK® 20/20e Defibrillator/Monitor. The atrium was identified by morphology and contraction sequence. Bipolar atrial wires were affixed (Medtronic temporary myocardial pacing wires, model number 6494). A bipolar electrogram was used to confirm placement, if needed. A surface electrogram was generated at a paper speed of 25 mm/sec and the atrium was exposed to an International Electrotechnical Commission 6LR61 alkaline battery to produce atrial fibrillation. Atrial fibrillation was confirmed on the surface electrogram, characterized as high-frequency, low-amplitude atrial electrograms, typically with varying R-R intervals. Because not every exposure to current induced atrial fibrillation, duration of exposure was measured for each attempt, measured as the number of seconds during which the atrial bipolar wires were exposed to the induction current. For each successful induction, atrial fibrillation duration was measured as the number of seconds after the end of induction while the atrium remained in fibrillation.

Cardiac Adhesion Assessment

Four weeks following pericardial abrasion and treatment, rabbits again underwent anesthesia and repeat sternotomy for the assessment of cardiac adhesion formation. Retrosternal scar tissue was observed by a blinded analyst and adhesion density at the apex, middle and base of the central epicardium was scored. The gross evaluation was evaluated with a 4 point scoring system (0-3). The scoring system indicated the following degree of adhesions 0: No Adhesions, 1: Mild Adhesions (easily dissected), 2: Moderate Adhesions and 3: Severe Adhesions (difficult to dissect). Right ventricular epicardial tissue samples were fixed in 10% formalin, paraffin embedded and hematoxylin-eosin stained for microscopic evaluation of NTF and adhesion formation. Thickness of NTF, as seen with Masson trichome staining, was observed by a blinded analyst with the National Institutes of Health Image program (version 1.62; National Institutes of Health, Springfield, Va.) to measure cardiac adhesion thickness.

Statistical Methods

All data are presented as mean±standard deviation. Normally-distributed data are compared by Student t test to analyze variance. Data that were not normally distributed were analyzed via Wilcoxon rank-sum test. A p value of less than 0.05 was considered significant. The primary outcome measure for arrhythmia was duration of atrial fibrillation per successful induction attempt. In addition, the number of attempts required to put rabbits into atrial fibrillation and duration of exposure to induction current was tabulated.

Results

Figure 6:
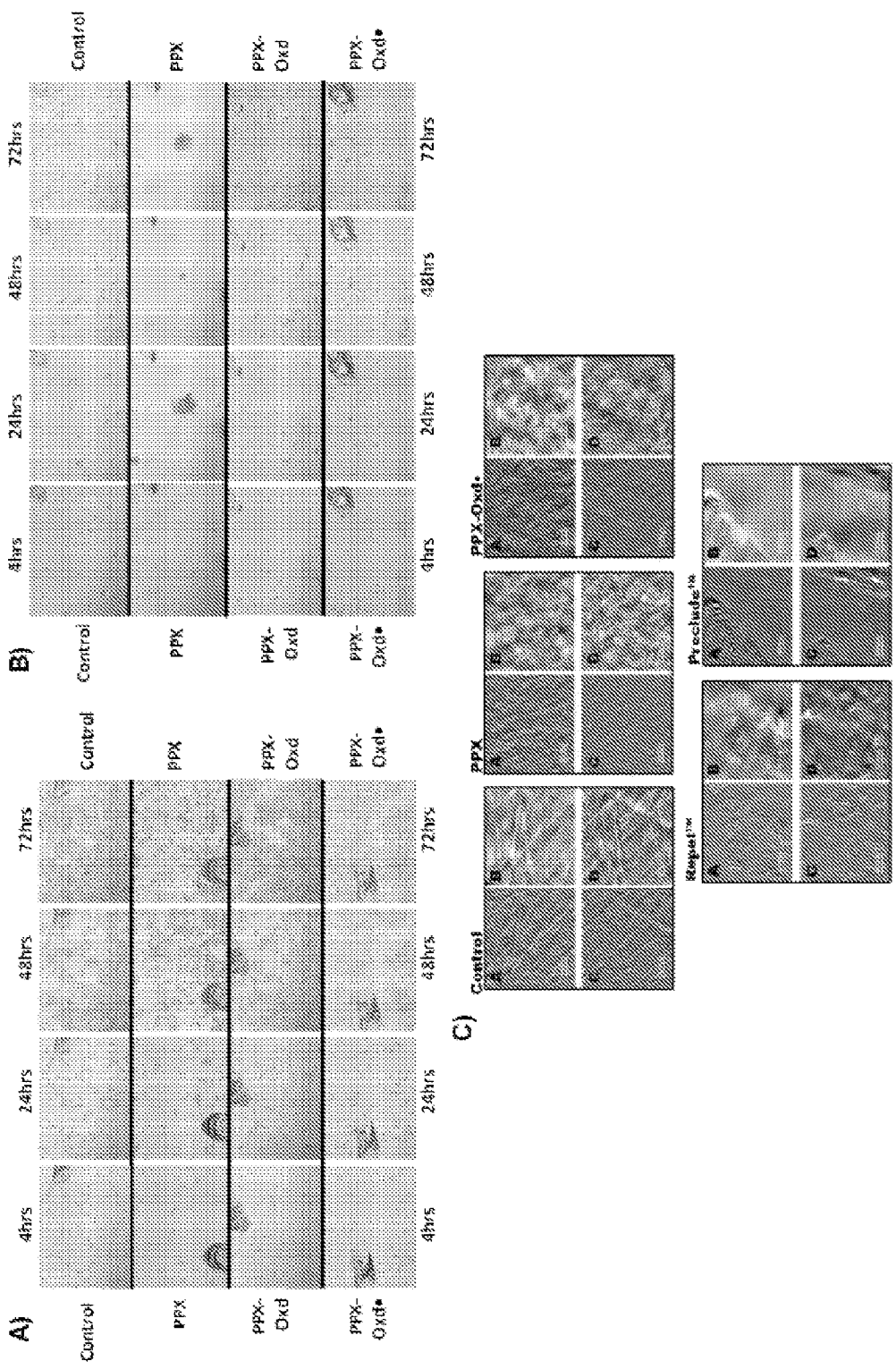
FIG. 6: Time lapse images of RAW264.7 murine macrophages A) grown on varying substrate surfaces over the course of 72 hrs (images taken at corresponding time points 4, 24, 48 and 72 hrs) as described in Example 1. As indicated by the Control surface RAW264.7 macrophages display comparative monolayer outgrowth on either of the oxidized PPX surfaces (PPX-Oxd, PPX-Oxd•). A somewhat irregular growth pattern is seen on PPX surfaces which did not undergo plasma oxidation. RAW264.7 macrophages were seeded at appropriate confluency to allow for maximum outgrowth on the third day. Cells were grown under standard conditions humidified air maintained at 37° C., 5% $CO^2$ supplemented with DMEM 10% FBS, 1% Pen/Strep. Time lapse images of 3T3-NIH murine fibroblasts B) grown on varying substrate surfaces over the course of 72 hrs (images taken at corresponding time points 4, 24, 48 and 72 hrs). As indicated by the Control surface 3T3-NIH fibroblasts display comparative monolayer outgrowth on either of the oxidized PPX surfaces (PPX-Oxd, PPX-Oxd•). Striking irregular growth patterns are evident on PPX surfaces which did not undergo plasma oxidation, lending to the assertion the fibroblasts were unable to adhere to the PPX surface. 3T3-NIH fibroblasts were seeded at appropriate confluency to allow for maximum outgrowth on the third day. Cells were grown under standard conditions humidified air maintained at 37° C., 5% $CO^2$ supplemented with DMEM 10% FBS, 1% Pen/Strep. Atomic Force Microscopy (AFM) images C) of surfaces (Control, PPX and PPX-Oxd) and films (Repel™ and Preclude™) under investigation. Image sets denoted by A & C reveal phase images compared to topographical outputs on B & D. Phase images reveal similar material properties across the surface. Uniform shading indicates the surface is composed of a similar material. Topographical images reflect changes in elevation across the film surface. Alterations in shading correspond to depressions or elevations across the film surface. Images A & B and C & D represent zoom in and zoom out functions respectively.
Figure 7:
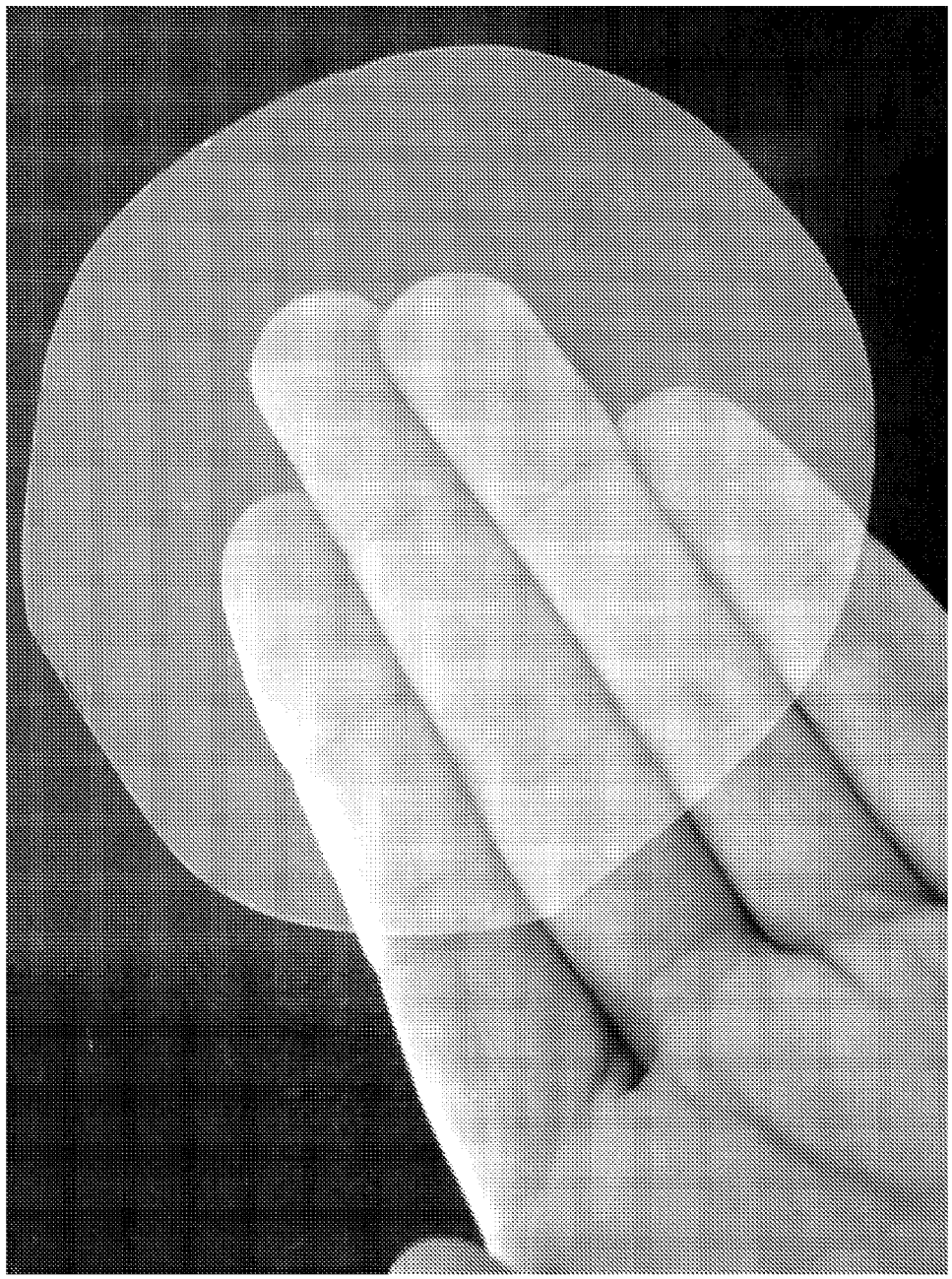
FIG. 7 shows an exemplary circular embodiment of the film of the present invention.
Figure 8:
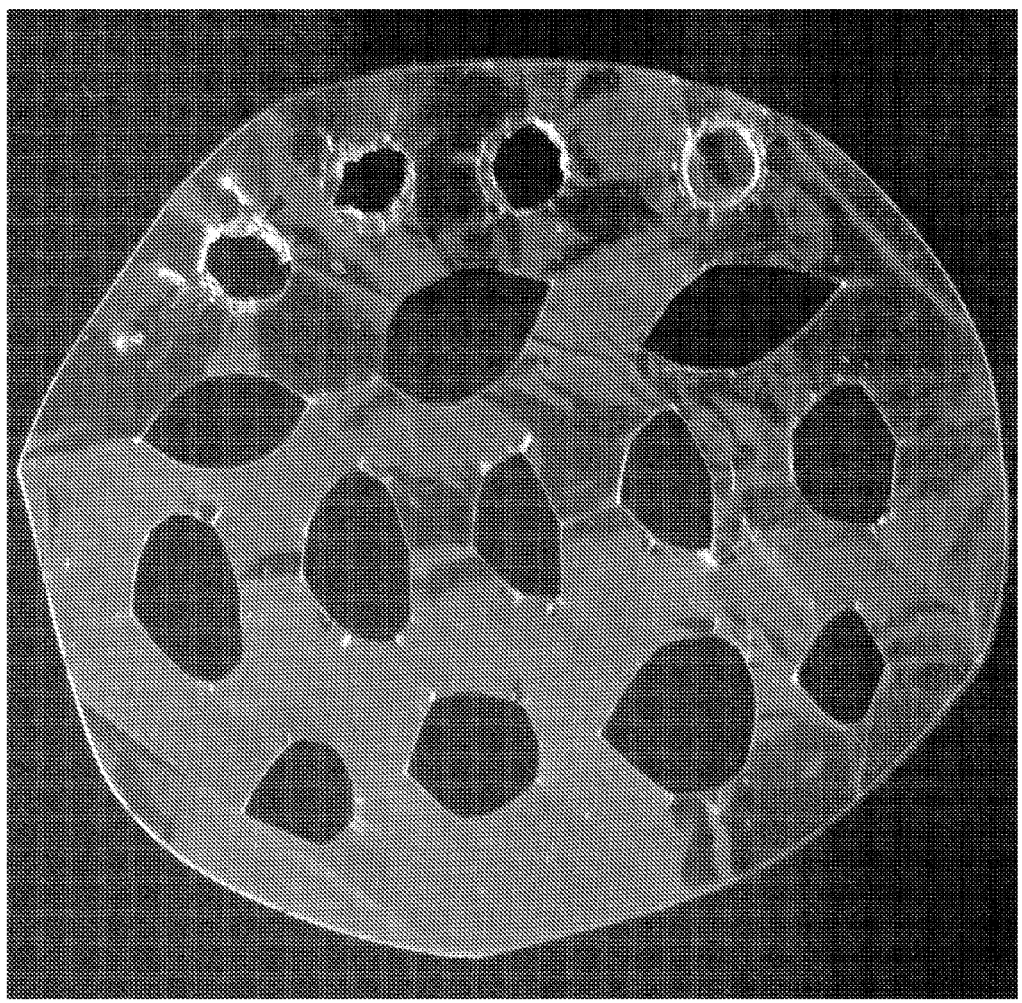
FIG. 8 shows an exemplary circular embodiment of the film of the present invention with various perforations, holes, and/or cut-outs.

An in-depth in-vitro response to PPX surfaces was completed to assess cellular interaction. To identify cellular response to the modified PPX surfaces, murine derived RAW264.7 macrophages (RAW) and 3T3-NIH fibroblasts (3T3) were seeded onto multi-well tissue growth plates previously deposited with varying PPX conditions (PPX-Oxd, PPX and PPX•) (•=unloaded PPX mesh deposition). Bright field images taken at time points of 4, 24, 48 and 72 hrs reveal the growth pattern of RAW and 3T3 cells on corresponding surfaces (FIG. 6A-B). PPX surfaces which had been modified via vacuum plasma treatment (PPX-Oxd and PPX-Oxd•) provided an interface conducive to monolayer cellular outgrowth of both RAW (FIG. 6A) and 3T3 cells (FIG. 6B) when compared to control surfaces (oxidized polystyrene, tissue culture plastic). Un-modified PPX surfaces (PPX) presented an interface less amenable to normative cellular outgrowth.

Figure 2:
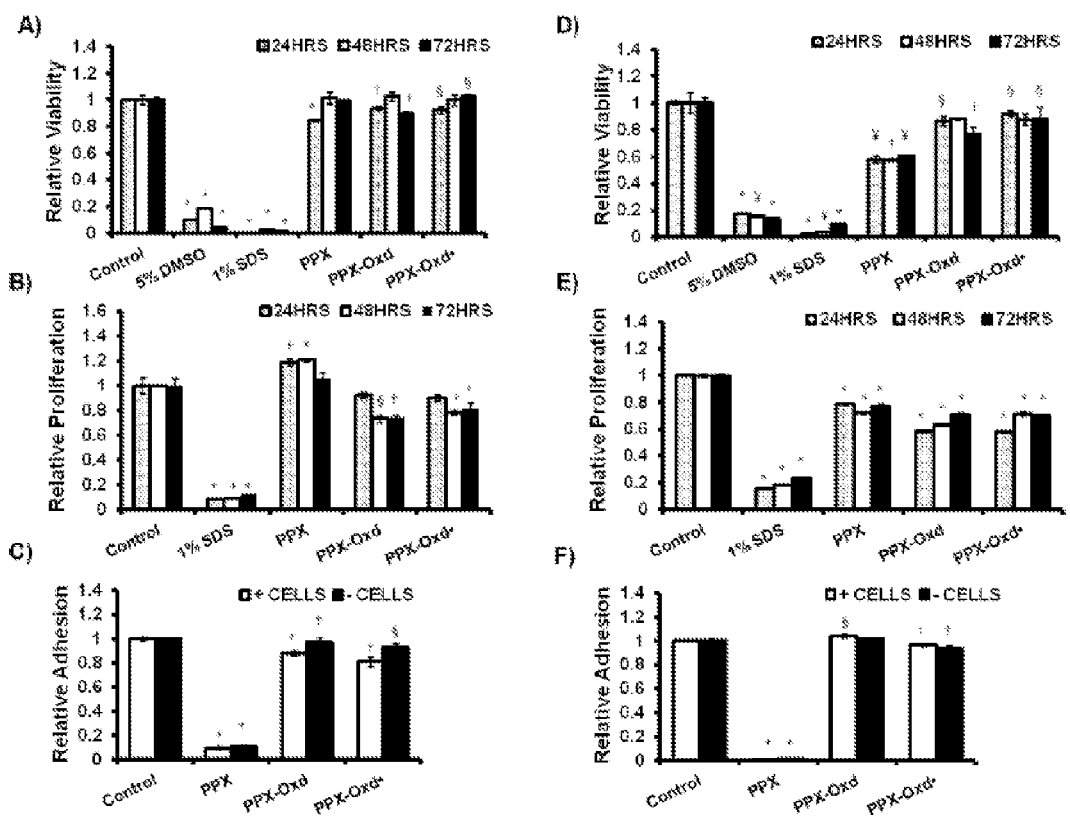
FIG. 2: Quantitative assessment of RAW264.7 macrophages on varying surfaces to determine cellular response as described in Example 1 below. A) Cellular viability of macrophages grown on Control and PPX surfaces over the respective time points. Further assays indicate B) proliferative ability of macrophages grown over time periods shown as well as an adhesion assay. Cellular interaction via an adhesion assay C) to PPX surfaces was performed with bare surfaces (–Cells) in addition to surfaces with a confluent monolayer of cells present (+Cells). Quantitative assessment of 3T3-NIH fibroblasts on varying surfaces to determine cellular response. D) Cellular viability of fibroblasts grown on Control and PPX surfaces over the respective time points. Further assays indicate E) proliferative ability of fibroblasts grown over time periods shown as well as an adhesion assay. Cellular interaction via an adhesion assay F) to PPX surfaces was performed with bare surfaces (–Cells) in addition to surfaces with a confluent monolayer of cells present (+Cells.)*$P<0.001$, †$P<0.01$, §$P<0.05$, ¥ $P<0.005$

Further cellular analysis was completed through the use of viability, proliferative and adhesion assays (FIG. 2). Viability assays were completed over the course of 24, 48 and 72 hour time points for each cell type (FIGS. 2A, D). RAW macrophages displayed little variation when seeded upon various PPX surfaces in reference to control surfaces. From a proliferative standpoint (FIG. 2B) there is a slight variation as it applies to the PPX surface, as there is a marginal increase in the proliferative capacity of the macrophages. This variation appears to be due to the inability of the macrophages to adhere to the surface of the PPX surface as noted by the adhesion assays performed (FIG. 2C). Alternatively, 3T3 fibroblasts revealed similar results as it pertains to PPX surfaces. Viability (FIG. 2D) was somewhat reduced, specifically as it applied to PPX surfaces. Combined with the bright field images of 3T3 cells (FIG. 6B) on PPX surfaces and the adhesion assays (FIG. 2F) completed, the decreased viability (FIG. 2D) could be the result of poor adhesion to the surface. Despite relative viability values comparable to controls, the proliferative capacity of 3T3 cells was reduced across most PPX modified surfaces (FIG. 2E).

Figure 3:
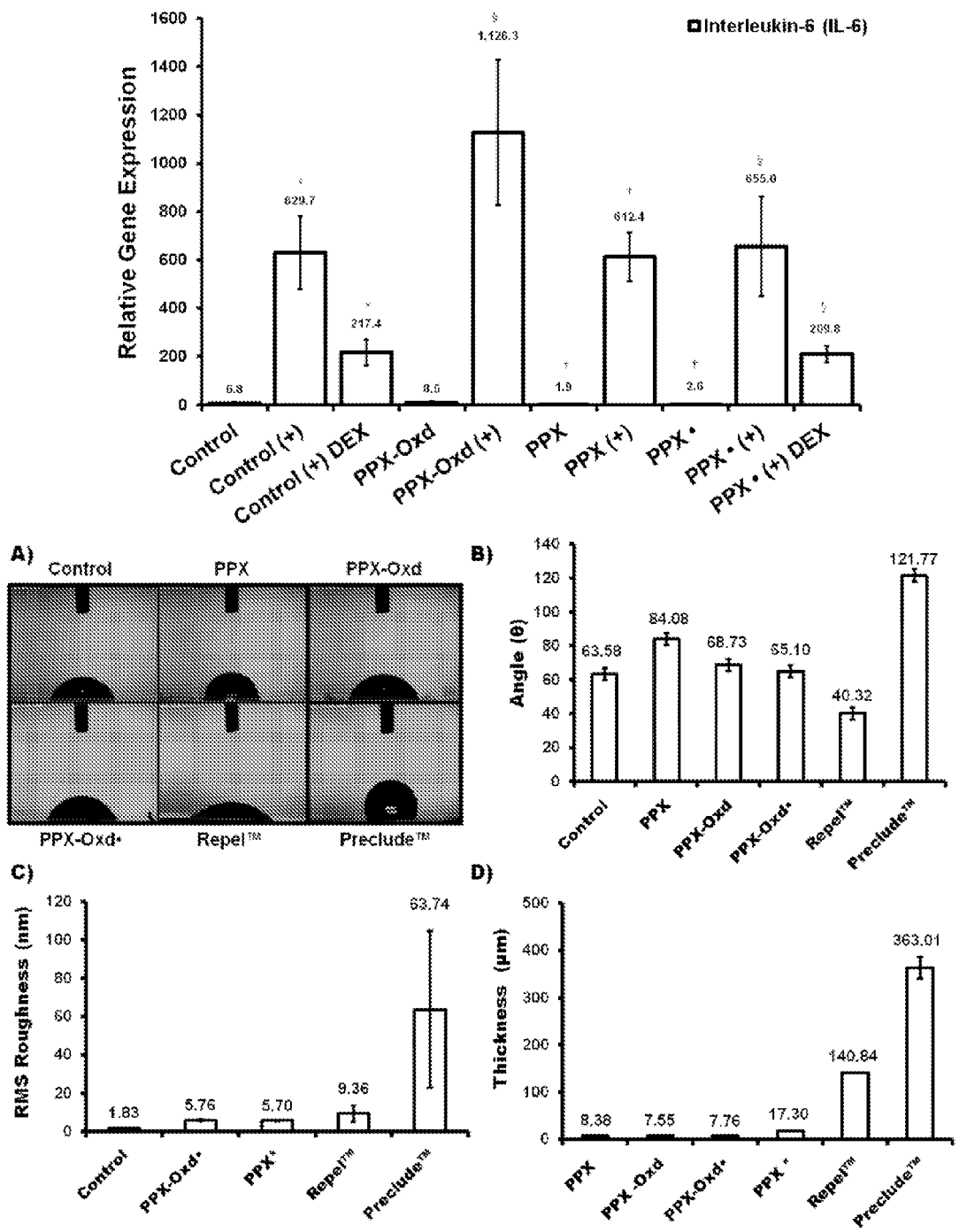
FIG. 3: RAW264.7 macrophage expression of IL-6 A) in response to PPX surfaces under examination as described in Example 1 below. Tissue culture plates (Control) were coated with PPX, modified accordingly (PPX-Oxd, PPX and PPX•) and then seeded with RAW264.7 macrophages. Baseline expression of IL-6 reveals modified and unmodified PPX surfaces do not increase IL-6 cytokine expression. Intentional inflammatory stimulation (+), with LPS, was completed to emphasize therapeutic response. Suppression of stimulated inflammation through DEX integration shows capacity of PPX film to locally deliver therapeutics. *$P<0.001$, †$P<0.01$, §$P<0.05$ Cross section images B) reveal relative surface wettability of each substrate. Angles obtained from image C) measurements show wettability characteristics of each substrate. Parylene (PPX) modified surfaces provide a contrasting effect of plasma oxidation on non-oxidized (PPX) and oxidized parylene (PPX-Oxd). Oxidation of PPX surfaces mimics wettability content of Control surfaces. Current surgical films (Repel™ and Preclude™) show contrasting levels of surface wettability. Surface feature measurements D) completed via AFM reveal RMS roughness of film surfaces compared to the Control surface. PPX films present a surface that is less rough when compared to Repel™ or Preclude™ which presents a relatively rough surface to cellular tissues. Further profile measurements E) which identify the thickness of each of the films examined, indicate PPX films provide a thinner profile when compared to surgical films Repel™ and Preclude™. *PPX deposition is 40 grams of Parylene-C
Figure 4:
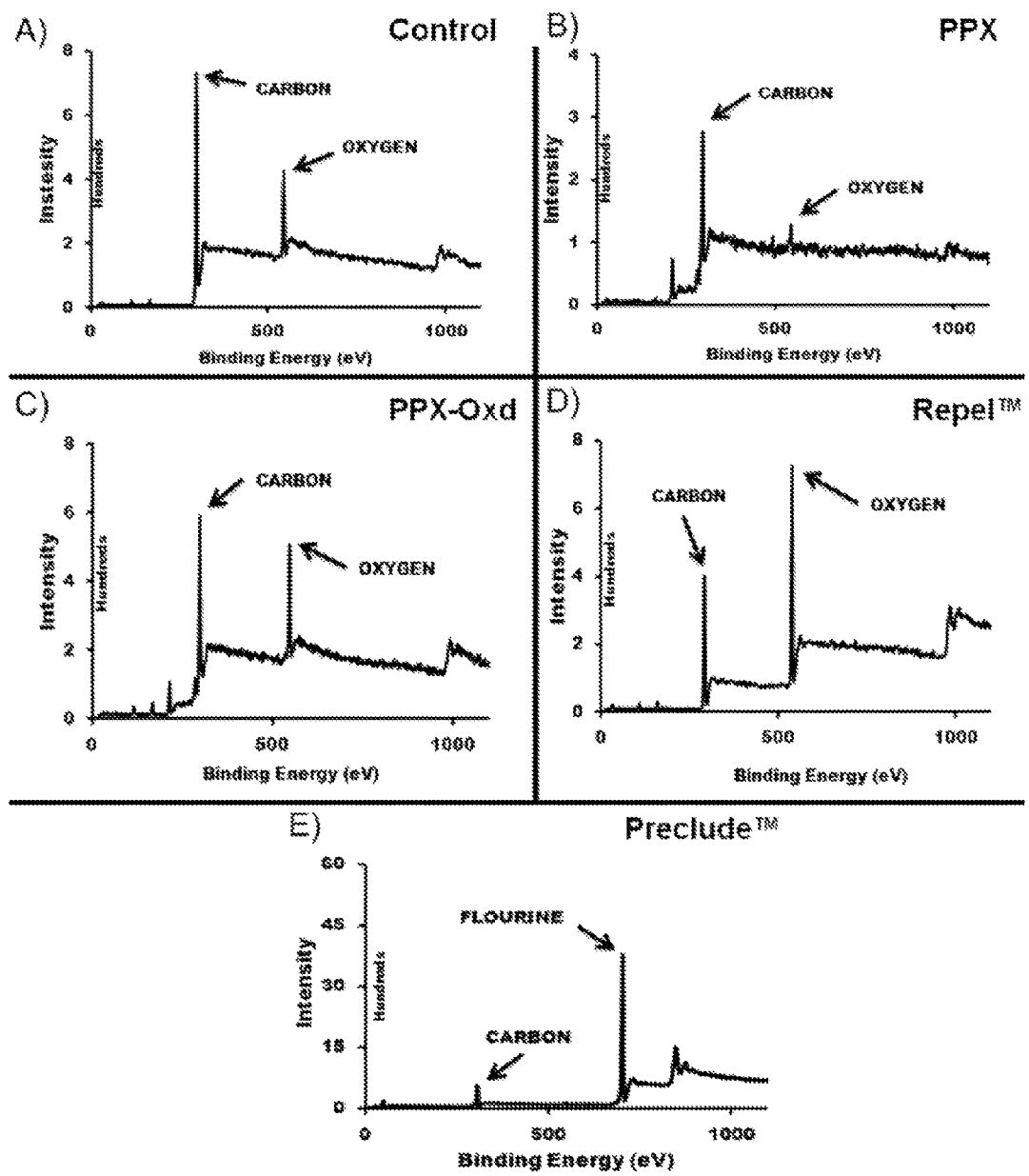
FIG. 4: X-Ray Photoelectron Spectroscopy (XPS) measurements identifying constituent elements present on substrate surfaces that were employed in Example 1 below. Elemental analysis revealed varying carbon and oxygen ratios as the primary elemental composition on each of the films, excluding the Preclude™ membrane. Control surfaces (A) revealed a greater degree of carbon to oxygen content. Comparatively, PPX (B) showed a decrease in oxygen content when compared to available carbon. Oxidized PPX (C) (PPX-Oxd) reveals an increase in oxygen which can be attributed to the oxygen plasma surface bombardment. It is of interest to note, the carbon/oxygen balance similarities between Control and PPX-Oxd substrates. The Repel™ (D) film is the only surface present whose oxygen content supersedes the amount of carbon present. Preclude™ (E) remaining the striking exception, as it contains a predominate amount of fluorine on the surface with negligible carbon content. FT-IR surface scans representing chemical species present on the surface of the respective films. F) Control surfaces, consisting of plasma oxidized polystyrene compared to various PPX conditions. G) Native PPX surface and H) oxidized PPX (PPX-Oxd) appear quite similar other than slight alterations in and around the 3000 cm$^{-1}$ peak. Repel™ I) and Preclude™ J) spectra are provided for comparison of current clinical anti-adhesive barriers.
Figure 4:
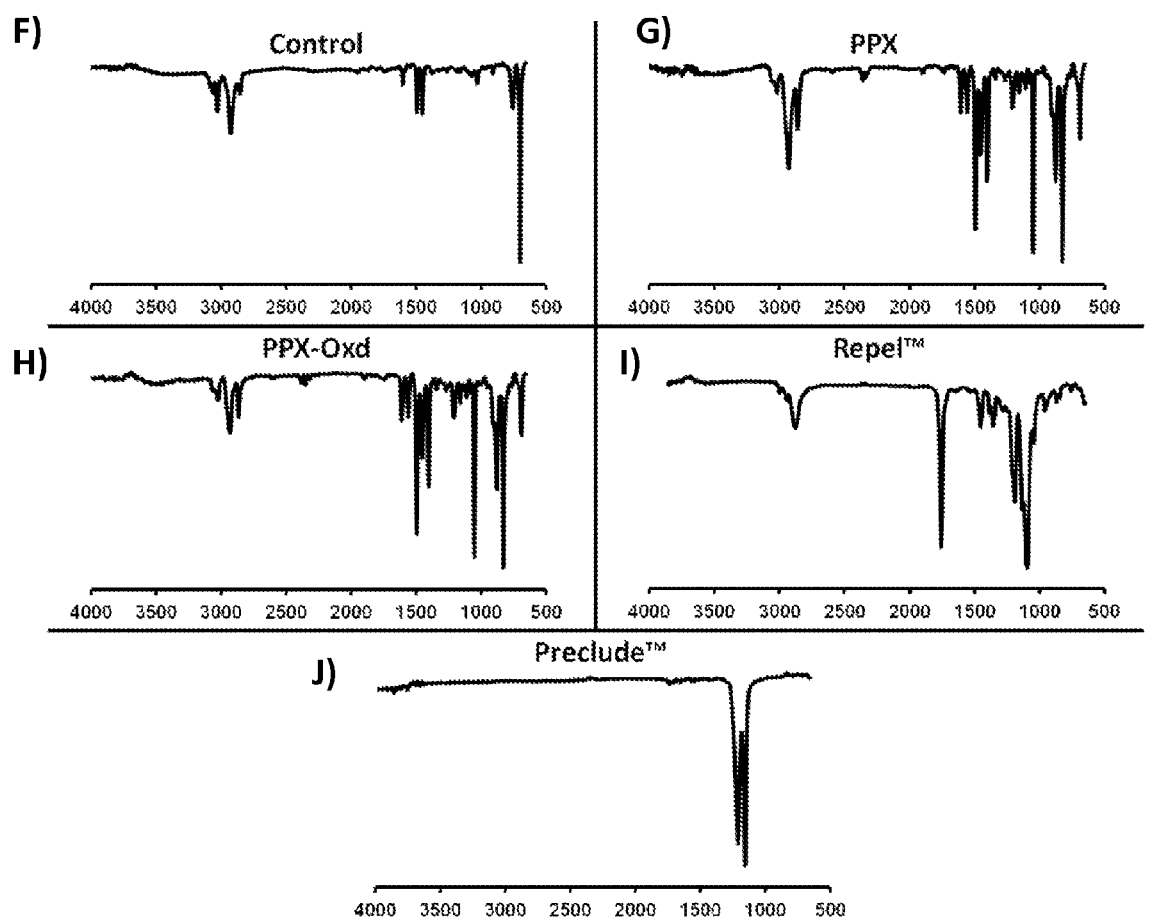

Gene expression, measuring the level of Interleukin-6 (IL-6) cytokine of RAW cells, further denotes capacity of PPX films to release sequestered therapeutic agents (FIG. 3A). Baseline results indicate all PPX surfaces (PPX-Oxd 8.6±7.3) (PPX 1.9±1.1 and PPX. 2.6±0.8, P<0.01) are well tolerated and do not impose further deleterious effects when compared to Control expression (6.8±4.5). Deliberate inflammation, through lipo-polysaccharide (LPS) stimulation (+) elevated expression levels of IL-6, Control (+) 629.7±150.1 (P<0.001), PPX-Oxd (+) 1,126.3±301.2 (P<0.05), PPX (+) 612.4±100.7 (P<0.01) and PPX•(+) 655.0±206.2 (P<0.05). DEX suppression of LPS stimulation reduces IL-6 expression when added to Controls (+) DEX 217.4±54.0 (P<0.001) or integrated into PPX films (PPX• (+) DEX 209.8±34.1 (P<0.05)). Surface and chemical analysis (FIGS. 3B-E & 4) completed on PPX surfaces in addition to current clinically available surgical barriers Repel™ and Preclude™ provided a basis for comparison. The balance of hydrophilic to hydrophobic content, or surface wettability, was obtained by measuring water contact angles (FIG. 3B-C). Native PPX surfaces displayed a mildly hydrophobic surface with angles of 84.08±1.33 compared to Control angles (63.58±0.62). Modified PPX surfaces PPX-Oxd and PPX-Oxd• demonstrated an increased hydrophilic surface from plasma oxidation, 68.73±1.88 and 65.10±2.08, respectively. Clinical films Repel™ and Preclude™ showed contrasting content, as Repel™ revealed an extremely hydrophilic surface, 40.32±2.39 compared to the very hydrophobic Preclude™ (121.77±3.64). AFM measurements examined surface roughness in nanometers (nm) (FIG. 3D) revealed topographical features among the various films examined. PPX surfaces showed uniform roughness across modified and unmodified surfaces, PPX-Oxd•5.76±0.51 nm and PPX 5.70±0.39 nm. Despite doubling the amount of polymer deposited (20 μm deposition PPX-Oxd• to 40 μm deposition PPX) no observable difference was noted in roughness values (5.76±0.51 nm to 5.70±0.39 nm). Comparatively, Repel™ and Preclude™ show contrasting roughness values. The resorbable Repel™ film revealed a consistent roughness of 9.36±4.35 nm; however, Preclude™ revealed a considerably high roughness value (63.74±40.78 nm) coupled with substantial variations across its surface. Film profile characterization in the form of thickness measurements are shown in microns (μm) (FIG. 3E). Modification of PPX films (PPX-Oxd and PPX-Oxd•) did not increase the film thickness compared to base PPX depositions, (7.55±0.20 μm and 7.76±0.07 μm to 8.38±0.09 μm). Due to the nature of plasma oxidation, the PPX surface is etched away during the process, thus resulting in the slight loss of surface material. Upon increasing the amount of PPX deposited, 20 gm to 40 μm there is a corresponding increase in film thickness, PPX*17.30±0.48 μm from PPX 8.38±0.09 μm. Repel and Preclude films revealed notably thicker profiles with values of 140.84±0.73 μm and 363.01±23.18 μm, respectively.

AFM images, shown in FIG. 6C depict surface features and compositional uniformity among the surfaces examined. Visualization of phase images, portions A & C, in FIG. 6C, reveal surfaces composed of uniform material, which was an expected result with the polymers under investigation. Images in B & D in FIG. 6C show topographical output as a measure of elevation changes across the films. This information was analyzed and interpreted previously in FIG. 3D as RMS roughness across each surface.

Chemical analysis identifying the predominant constituent elements within each film was measured through XPS (FIG. 4A-E). Modification of PPX surfaces (PPX-Oxd) (FIG. 4C) show the impact of plasma oxidation in regard to the change in oxygen content from native PPX (FIG. 4B). Compared to the elemental content of control surfaces, which are considered biocompatible (FIG. 4A), modified PPX (PPX-Oxd) surfaces bear a striking resemblance in carbon to oxygen ratios. The Repel™ film (FIG. 4D) displayed an opposing ratio of carbon to oxygen content, whereby oxygen surpassed the carbon present. Contrastingly, the Preclude™ (FIG. 4E) membrane did not contain the typical oxygen carbon relationship a, but consisted mainly of fluorine with traces of carbon.

FIG. 4F-J depicts FT-IR analysis revealing chemical groups present on each of the film surfaces. Examination of results obtained depict subtle changes to PPX modified films (PPX-Oxd) (FIG. 14H) when compared to native PPX (FIG. 4G) surfaces, specifically in and around the 3000 $cm^{-1}$ peak. Plasma oxidation is a common method of prepping control surfaces for cellular compatibility which would appear to slightly affect the carbon-hydrogen arrangement of the aromatic backbone of either polymer. Repel™ and Preclude™ readouts correspond to their chemical composition shown FIG. 4I-J.

In Vivo Testing

Figure 5:
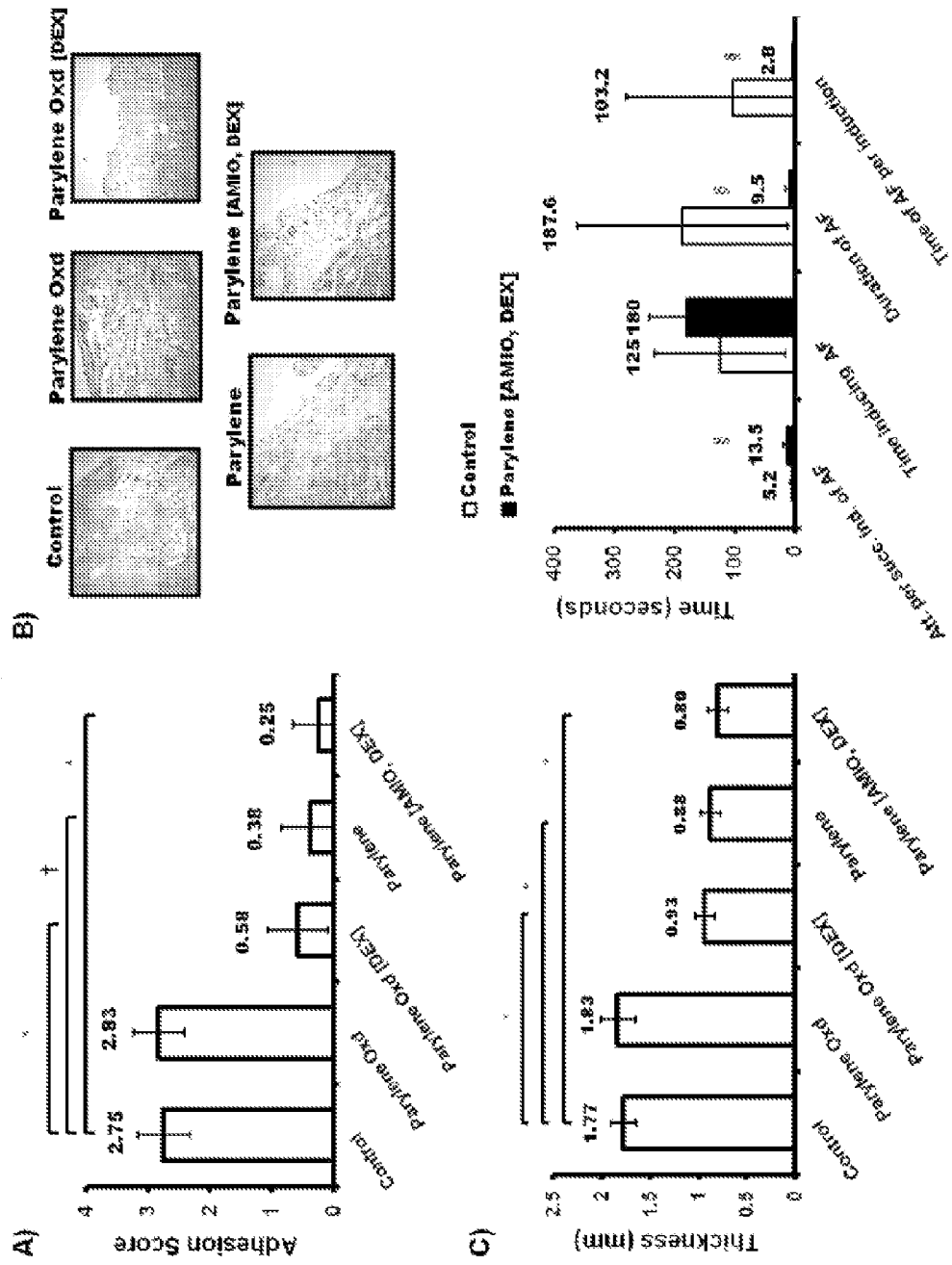
FIG. 5: This figure presents in vivo results from Example 1 below. The extent of perioperative inflammation represented as adhesion scores A) to implanted PPX films. 3 point scoring system depicting level of inflammation and scarring which occurred, 0: No Adhesions, 1: Filmy Adhesions, 2: Moderate Adhesions 3: Severe Adhesions. Therapeutic involvement decreased inflammation related adhesions considerably (PPX-Oxd[DEX] and PPX[AMIO, DEX] films compared to Control. Native PPX films without drug prevented adhesion formation due to inherent material properties. Alteration of PPX films through surface oxidation (PPX-Oxd) incited severe inflammation as noted by an increase in adhesion formation.*P<0.001, †P<0.01 Tissue section staining B) reveal level of scarring and cellular infiltration, respectively. Level of sustained inflammation is apparent in Control and PPX-Oxd samples from the extent of NTF formation and cell density. Reduced infiltrates are noted in PPX-Oxd[DEX] and PPX[AMIO, DEX] samples a result of locally delivered DEX. PPX alone displayed cellular infiltrates greater than DEX infused films, but less than Control or modified PPX surfaces. Tissue analysis C) reveals NTF thickness as a result of perioperative inflammation. Thickness measurements of NTF correlate to levels of inflammation at the time of resternotomy. PPX films integrated with DEX showed less NTF compared to Control and PPX-Oxd films. Contrastingly, PPX alone showed fibrosis thickness similar to that of DEX infused films. *P<0.001 Atrial fibrillation experiments (D) underscore the ability for a PPX film to reduce entrance into and duration of AF when loaded with AMIO and delivered locally. §P<0.05

After sternotomy and adhesion treatment, the heart of 30 rabbits was treated based on the randomized assigned group: Control group, oxidized PPX (PPX-Oxd), PPX-Oxd infused with DEX (PPX-Oxd[DEX]), native PPX (PPX), and PPX infused with DEX and AMIO (PPX[AMIO, DEX]). Two rabbits had a technical issue early on with displacement of the endotracheal tube during the operation which led to death. One Control rabbit was undergoing electrophysiologic testing at the time of inadvertant endotracheal displacement and as a result only had a single (successful) arrhythmia induction attempt. Thus, 28 rabbits (93%) survived the initial surgery with no postoperative complications. After 4 weeks, surviving rabbits (93%) were intubated, a repeat sternotomy was performed to observe and quantify the presence of inflammation, adhesions and measure arrhythmia induction (FIG. 5).

Gross Examination

In the Control group, highly dense adhesions formed throughout the retrosternal region between the epicardium and the sternum which resulted in difficult dissection between the sternum and epicardium, leading to injury to the myocardium in some rabbits. In contrast, visually less dense adhesions were present in the PPX, PPX-Oxd[DEX], and PPX [AMIO, DEX] with a clear, smooth epicardium that facilitated dissection. Some rabbits appeared to lack any adhesions, similar to the appearance at the initial sternotomy. In the PPX-Oxd group, the adhesions formed were nearly similar and dense as present in the Control group. Control rabbits exhibited tenacious adhesion formation resulting in an adhesion score of 2.75±0.42. PPX films, loaded with DEX exhibited a decrease in adhesion scores compared to Controls (PPX-Oxd[DEX] 0.58±0.49 and PPX[AMIO, DEX] 0.25±0.42). Adhesion scores for PPX films alone, modified PPX-Oxd and unmodified PPX show contrasting results due to surface modification of each respective film (PPX-Oxd 2.83±0.41 vs. PPX 0.38±0.48, P<0.01) None of the groups had adhesions located at the posterior or lateral portions of the heart. Furthermore, the regional distribution of the adhesions within the heart was uniform between the apex, middle, and base of the heart.

Microscopic Analysis

All specimens had a neotissue fibrosis (NTF) layer compromised of collagen and adipose tissue that formed upon the myocardium (FIG. 5B-C). Tissue sections display efficacy of integrated therapeutic DEX and cellular response to PPX films (FIG. 5B-C). Control and PPX-Oxd images reveal significant cellular infiltration indicative of a chronic inflammatory response (FIG. 5B) in addition to the formation of a prominent NTF, 1.78±0.13 mm and 1.83±0.17 mm respectively (FIG. 5C). DEX integrated PPX films, (PPX-Oxd [DEX], PPX [AMIO, DEX]); exhibited a reduced cellular infiltration in addition to diminished NTF formation, 0.93±0.09 mm and 0.80±0.10 mm (P<0.001) respectively. Conversely, native PPX films displayed a dense cell infiltration lending to a sustained inflammatory response (FIG. 5B); however, subsequent NTF formation was comparable (0.88±0.10 mm, P<0.001) to DEX infused films (FIG. 5C). This information lends precedence to the ability of PPX to separate contiguous tissue surfaces effectively, reducing adhesion formation, despite persistent inflammation.

Electrophysiology Studies

A total of 13 out of 30 rabbits underwent electrophysiologic testing. The primary arrhythmia outcome was duration of atrial fibrillation (AF) per successful induction. Rabbits with PPX[AMIO, DEX] (n=6) films sustained atrial fibrillation for a 2.8 seconds (±1.2 sec) per successful induction versus 103.2 seconds (±178 sec) in Control rabbits (p=0.004) (n=7). More attempts per successful induction were required to induce atrial fibrillation in rabbits with PPX[AMIO, DEX] films than rabbits with Control films (13.5±7.0 vs. 5.2±4.3 attempts per successful induction, p=0.04). The duration of atrial fibrillation per rabbit was lower in PPX[AMIO, DEX] rabbits than in Control rabbits (9.5±6.8 sec vs. 187.6±174.7 sec of atrial fibrillation per rabbit, p=0.003). Rabbits with PPX[AMIO, DEX] films and Control rabbits did not differ in the total time each rabbit was exposed to induction current (180±63 vs. 125±109 seconds, p=0.253), suggesting that both populations had equally rigorous attempts at arrhythmia induction. One rabbit with a PPX[AMIO, DEX] film was not inducible for atrial fibrillation after 32 induction attempts. A PPX[AMIO, DEX] rabbit without inducible AF is supportive of the fact that the PPX[AMIO, DEX] film is protective against atrial fibrillation. If this rabbit were included, it would strengthen the findings; however, because no arrhythmia was induced, this rabbit was excluded from analysis of arrhythmia.

Discussion

In-vitro assessment of PPX surfaces by time lapse images (FIGS. 6A-B), viability (FIGS. 2A, D), proliferation assays (FIGS. 2B, E) and IL-6 gene expression (FIG. 3A) lend support to PPX variants as biocompatible interfaces. From a cellular standpoint, unmodified PPX films prevented or inhibited complete interaction of either cell line examined. These results are confirmed via adhesion assays completed (FIGS. 2C, F). The inability of macrophage or fibroblast adherence to the surface correlates to a diminished capacity of in-vivo tissues from interacting or adhering to the PPX film, thereby preventing the onset of adhesion formation. This aspect lends precedence to the ability of PPX films to respond accordingly when implanted in-vivo. Consequently, those surfaces which facilitated adhesion may sustain the inflammatory response and result in the formation of adhesions. Film surfaces modified to reduce or prevent cellular involvement may allow for proper regeneration of damaged tissues while inhibiting adhesion formation. Cytokine expression (FIG. 3A) of Interleukin-6 (IL-6) reflects the impact of therapeutic integration in PPX films. Integration of DEX and subsequent release reveal the suppression of intentional inflammation, through lipo-polysaccharide (LPS) induction. Decreasing IL-6 expression across DEX samples exemplify the therapeutic potential of drug integration. Furthermore, basal expression of IL-6 on Control and various PPX films, indicate the compatibility of macrophages upon each surface.

Comparative chemical analysis of species present on each surface identified certain chemical groups which may be conducive in preventing tissue adhesion. Data obtained (FIG. 3B-C) indicate a moderate degree of hydrophobic content (PPX angles 84.08±1.33), appears to impede cellular or tissue interaction to the film surface. Alternatively, modification of similar PPX surfaces when oxidized (PPX-Oxd) increased the extent of hydrophilic groups (PPX-Oxd angle 68.73±1.88). The increase in hydrophilic content is directly attributed to an increase in oxygen on the surface (FIG. 4C). Such surface alteration leads to profound changes in cellular growth and adhesion patterns, as noted in FIGS. 6A-B, 2C, and F. Modification through plasma oxidation increasing oxygen content appears to alter cellular response.

Additional physical properties measured included surface roughness (FIG. 3D) and film thickness (FIG. 3E). Native PPX films present smooth surfaces and a thinner profile when compared to clinical films Repel™ and Preclude™. Each PPX surface, PPX-Oxd and PPX, presented similar roughness values 5.76±0.51 nm to 5.70±0.39 nm. Additionally, changes in material bulk properties may impact the inflammatory and/or healing response. Subsequent reduction in implanted material or bulk profiles can be considered beneficial as to lessen the disturbance to the surrounding tissue architecture.

The PPX film infused with DEX significantly reduced the extent of inflammation, (FIG. 5A, PPX-Oxd[DEX] 0.58±0.49 and PPX [AMIO, DEX] 0.25±0.42 (P<0.001)) interpreted via adhesion formation, when compared to Control animals 2.75±0.42. This reduction in inflammation may be attributed to DEX release from the PPX film. As noted with modified PPX surfaces, oxidized PPX (PPX-Oxd) caused substantial adhesions (2.83±0.41). Oxidation of the surface allowed for tissue adherence, affirmed by in-vitro data, during periods of inflammation which was inhibited through local DEX administration. Surface modification or chemical composition may exert an influence upon inflammation of tissue surfaces as it relates to adhesion formation. Unmodified PPX surfaces, revealed a significant reduction in adhesion score 0.38±0.48 (P<0.01) without therapeutic involvement. Thus, native PPX surfaces present a surface ideal for the reduction of sustained perioperative inflammation. Tissue interaction or adherence to an implanted barrier appears to directly lead to or perpetuate the inflammatory response resulting in the formation of adhesions. Thus fabrication of a material surface which inhibits tissue interaction coupled with the gradual release of an anti-inflammatory could have a profound effect at reducing chronic perioperative related inflammation.

Tissue sections obtained from each condition examined revealed inflammation trends (FIG. 5B-C) corresponding to reported adhesion scores. Infusion of DEX into PPX films, PPX-Oxd[DEX] and PPX[AMIO, DEX], resulted in minimal cellular infiltration (FIG. 5B) or inflammation correlating to NTF thickness (FIG. 5C) values of 0.93±0.09 mm and 0.80±0.10 mm, respectively. In contrast, PPX-Oxd and Control animals revealed significant cellular infiltration with subsequent corresponding NTF thickness measurements of 1.78±0.13 mm and 1.83±0.17 mm. Native PPX films implanted without DEX appear to sustain a subdued level of inflammation represented by cellular infiltration remaining at time of resternotomy (FIG. 5B). However, NTF formation is reduced, 0.88±0.10 mm, (FIG. 5C) due to the film preventing interaction of opposing tissue surfaces. These results indicate the capacity of an anti-adhesive barrier, which does not promote or interact with tissue surfaces, to prevent chronic perioperative adhesions in lieu of therapeutic involvement. Historically, the most common means of preventing acute perioperative inflammation is the transient separation of contiguous tissue surfaces with resorbable barriers. However, this methodology does not appear to adequately reduce chronic perioperative inflammation. The presence of a non-resorbable barrier which inhibits cellular interaction of opposing tissues can significantly inhibit the onset of chronic inflammation and allow for proper mesothelial response and repair at the site of injury.

Postoperative atrial fibrillation continues to complicate surgical intervention. Systemic amiodarone has been used as a peri-operative therapy; however, concerns of systemic toxicity remain and releasing AMIO in a site specific manner may be a more effective method of delivery.31-31. Preferably, localized delivery via a DDP would reduce toxicity concerns of systemic injection. Atrial fibrillation was more difficult to induce in rabbits with PPX[AMIO, DEX] films and more difficult to sustain (FIG. 5D). These results indicate the ability of PPX films to deliver a drug to the heart, thereby reducing entrance into and duration of AF events as they might occur postoperatively.

In certain embodiments, the PPX film targets two major complications of cardiac surgery in a combinatorial fashion through the delivery of targeted therapeutics to the applied organ diminishing the necessity for intravenous infusion. The nano-structured film allows for the efficient release of therapeutics (e.g., DEX and AMIO) and remains as a protective barrier between the heart and chest cavity. Reduction of surgical complications through application of novel nano-structured PPX film successfully suppressed peri-operative inflammation as well as atrial fibrillation. As such, a PPX loaded device is a potent tool for clinicians to mitigate these challenges. This intervention is accomplished via twofold mechanisms of a physical barrier in addition to the release of therapeutic agents. Additionally, it employs physical characteristics which inhibit adhesion of fibrotic tissues to the surface of the film, while also allowing for visualization of underlying tissue.

REFERENCES

1. Speir, A. M., Kasirajan, V., Barnett, S. D. & Former, E., Jr. Additive Costs of Postoperative Complications for Isolated Coronary Artery Bypass Grafting Patients in Virginia. Annals of Thoracic Surgery 88, 40-46 (2009).
2. Price, J. D., Romeiser, J. L., Gnerre, J. M., Shroyer, A. L. W. & Rosengart, T. K. Risk Analysis for Readmission after Coronary Artery Bypass Surgery: Developing a Strategy to Reduce Readmissions. Journal of the American College of Surgeons.
3. Aviles, R. J. et al. Inflammation as a risk factor for atrial fibrillation. Circulation 108, 3006-3010 (2003).
4. Guo, Y., Lip, G. Y. H. & Apostolakis, S. Inflammation in Atrial Fibrillation. Journal of the American College of Cardiology 60, 2263-2270 (2012).
5. Halonen, J. et al. Corticosteroids for the prevention of atrial fibrillation after cardiac surgery—A randomized controlled trial. Jama-Journal of the American Medical Association 297, 1562-1567 (2007).
6. Imazio, M. et al. Colchicine Reduces Postoperative Atrial Fibrillation Results of the Colchicine for the Prevention of the Postpericardiotomy Syndrome (COPPS) Atrial Fibrillation Substudy. Circulation 124, 2290-U2258 (2011).
7. Imazio, M. et al. Colchicine prevents early postoperative pericardial and pleural effusions. American Heart Journal 162, 527-U149 (2011).
8. Deftereos, S. et al. Colchicine for Prevention of Early Atrial Fibrillation Recurrence After Pulmonary Vein Isolation A Randomized Controlled Study. Journal of the American College of Cardiology 60, 1790-1796 (2012).
9. Chen, M. et al. Parylene-Encapsulated Copolymeric Membranes as Localized and Sustained Drug Delivery Platforms Annals of Biomedical Engineering 37, 2003-2017 (2009).
10. Lam, R. et al. Nanodiamond-Embedded Microfilm Devices for Localized Chemotherapeutic Elution. Acs Nano 2, 2095-2102 (2008).
11. Pierstorff, E., Lam, R. & Ho, D. Nanoscale architectural tuning of parylene patch devices to control therapeutic release rates. Nanotechnology 19 (2008).
12. Robinson, E. M., Lam, R., Pierstorff, E. D. & Ho, D. Localized Therapeutic Release via an Amine-Functionalized Poly-p-xylene Microfilm Device. The Journal of Physical Chemistry B 112, 11451-11455 (2008).
13. Boduroglu, S., Cetinkaya, M., Dressick, W. J., Singh, A. & Demirel, M. C. Controlling the Wettability and Adhesion of Nanostructured Poly-(p-xylylene) Films. Langmuir 23, 11391-11395 (2007).
14. Horcas, I. et al. WSXM: A software for scanning probe microscopy and a tool for nanotechnology. Review of Scientific Instruments 78 (2007).
15. Walther, T. et al. A novel adhesion barrier facilitates reoperations in complex congenital cardiac surgery. Journal of Thoracic and Cardiovascular Surgery 129, 359-363 (2005).
16. Schreiber, C. et al. European clinical experience with REPEL-CV (R). Expert Review of Medical Devices 4, 291-295 (2007).
17. Mitchell, J., Lee, R., Neya, K. & Vlahakes, G. Reduction in experimental pericardial adhesions using a hyaluronic acid bioabsorbable membrane. Eur J Cardiothorac Surg 8, 149-152 (1994).
18. Sakuma, K., Iguchi, A., Ikada, Y. & Tabayashi, K. Closure of the pericardium using synthetic bioabsorbable polymers Annals of Thoracic Surgery 80, 1835-1840 (2005).
19. Lodge, A. J. et al. A Novel Bioresorbable Film Reduces Postoperative Adhesions After Infant Cardiac Surgery. The Annals of Thoracic Surgery 86, 614-621 (2008).
20. Alpay, Z. et al. Altered in vitro immune response to hypoxia-treated normal peritoneal fibroblasts. Fertility and Sterility 87, 426-429 (2007).
21. Saed, G. M. & Diamond, M. P. Molecular Characterization of Postoperative Adhesions: The Adhesion Phenotype. The Journal of the American Association of Gynecologic Laparoscopists 11, 307-314 (2004).
22. Saed, G. M. & Diamond, M. P. Apoptosis and proliferation of human peritoneal fibroblasts in response to hypoxia. Fertility and Sterility 78, 137-143 (2002).
23. Saed, G. M. & Diamond, M. P. Hypoxia-induced irreversible up-regulation of type I collagen and transforming growth factor-beta 1 in human peritoneal fibroblasts. Fertility and Sterility 78, 144-147 (2002).
24. Saed, G. M., Zhang, W. & Diamond, M. P. Molecular characterization of fibroblasts isolated from human peritoneum and adhesions. Fertility and Sterility 75, 763-768 (2001).
25. diZeregal, G. S. & Campeau, J. D. Peritoneal repair and post-surgical adhesion formation. Human Reproduction Update 7, 547-555 (2001).
26. Cheong, Y. C. et al. Peritoneal healing and adhesion formation/reformation. Human Reproduction Update 7, 556-566 (2001).
27. Alizzi, A. M. et al. Reduction of Post-surgical Pericardial Adhesions Using a Pig Model. Heart Lung and Circulation 21, 22-29 (2012).
28. Chang, Y. et al. Mesothelium regeneration on acellular bovine pericardia loaded with an angiogenic agent (ginsenoside Rg(1)) successfully reduces postsurgical pericardial adhesions. Journal of Thoracic and Cardiovascular Surgery 132, 867-U874 (2006).
29. Andersson, A. S. et al. Nanoscale features influence epithelial cell morphology and cytokine production. Biomaterials 24, 3427-3436 (2003).
30. Mohiuddin, M., Pan, H.-A., Hung, Y.-C. & Huang, G. S. Control of growth and inflammatory response of macrophages and foam cells with nanotopography. Nanoscale Research Letters 7, 1-9 (2012).
31. Bagshaw, S. M. et al. Prophylactic amiodarone for prevention of atrial fibrillation after cardiac surgery: A meta-analysis Annals of Thoracic Surgery 82, 1927-1937 (2006).
32. Bolderman, R. W. et al. Epicardial application of an amiodarone-releasing hydrogel to suppress atrial tachyarrhythmias. International Journal of Cardiology 149, 341-346 (2011).
33. Sun, Q. et al. Sustained Release of Multiple Growth Factors from Injectable Polymeric System as a Novel Therapeutic Approach Towards Angiogenesis. Pharm Res 27, 264-271 (2010).
34. Stevenson, C. L., Santini Jr, J. T. & Langer, R. Reservoir-based drug delivery systems utilizing microtechnology. Advanced Drug Delivery Reviews 64, 1590-1602 (2012).
35. Lin, C.-C., Metters, A. T. & Anseth, K. S. Functional PEG—peptide hydrogels to modulate local inflammation induced by the pro-inflammatory cytokine TNFα. Biomaterials 30, 4907-4914 (2009).

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. An article of manufacture consisting essentially of: a polymer film with a top surface and a bottom surface,
   wherein said polymer film consists essentially of a para-xylene polymer,
   wherein said polymer film has a thickness between 1 μm and 75 μm,
   wherein substantially all of said top surface has a water contact angle between 75 and 95 degrees and is non-adherent to tissue,
   wherein substantially all of said bottom surface has a water contact angle between 75 and 95 degrees and is non-adherent to tissue, and
   wherein said polymer film is sterilized and sized to serve as a tissue separator and/or adhesion barrier in a subject.

2. The article of manufacture of claim 1, wherein substantially all of said top surface is non-oxidized.

3. The article of manufacture of claim 1, wherein said top surface has a carbon to oxygen ratio of about 2:1 to about 18:1.

4. The article of manufacture of claim 1, wherein said top surface has a RMS roughness of about 1.0 nm to about 10.0 nm.

5. The article of manufacture of claim 1, wherein said top surface of said polymer film has a surface area between 10 cm² and 400 cm².

6. The article of manufacture of claim 1, wherein para-xylene polymer comprises parylene C.

7. The article of manufacture of claim 1, wherein said para-xylene polymer is selected from the group consisting of: parylene A, parylene AM, parylene AF4, parylene SF, parylene HT, parylene X, parylene N, and parylene D.

8. The article of manufacture of claim 1, wherein said subject is a human.

9. The article of manufacture of claim 1, wherein substantially all of said bottom surface is non-oxidized.

10. The article of manufacture of claim 9, wherein substantially all of said bottom surface has a Carbon to Oxygen ratio range of about 2:1 to 18:1 and RMS roughness between about 1.0 nm and 10.0 nm.

11. The article of manufacture of claim 1, wherein said polymer film has a thickness between 5 μm and 25 μm.

12. A method for separating areas in an internal region of a subject comprising:
   inserting an article of manufacture into an internal region of a subject between first and second areas,
   wherein said article of manufacture is as recited in claim 1.

13. A system comprising:
   a) an article of manufacture as recited in claim 1, and
   b) a packaging component, wherein said article of manufacture is located inside said packaging component.

14. The system of claim 13, wherein said article of manufacture is sealed inside said packaging component such that said article of manufacture remains sterile while inside said packaging component.

* * * * *